United States Patent
Sherrill et al.

(10) Patent No.: US 9,598,956 B2
(45) Date of Patent: *Mar. 21, 2017

(54) SYSTEMS AND METHODS OF A SAMPLE BOTTLE ASSEMBLY

(71) Applicant: Halliburton Energy Services, Inc., Houston, TX (US)

(72) Inventors: Kristopher V. Sherrill, Humble, TX (US); Clive D. Menezes, Conroe, TX (US); David Welshans, Damon, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 60 days.

This patent is subject to a terminal disclaimer.

(21) Appl. No.: 14/734,442

(22) Filed: Jun. 9, 2015

(65) Prior Publication Data

US 2015/0275662 A1    Oct. 1, 2015

Related U.S. Application Data

(63) Continuation of application No. 13/580,104, filed as application No. PCT/US2010/024843 on Feb. 20, 2010, now Pat. No. 9,068,405.

(51) Int. Cl.
*E21B 17/16* (2006.01)
*E21B 47/01* (2012.01)
(Continued)

(52) U.S. Cl.
CPC ............ *E21B 49/081* (2013.01); *E21B 17/16* (2013.01); *E21B 47/01* (2013.01); *E21B 49/08* (2013.01);
(Continued)

(58) Field of Classification Search
CPC .......... E21B 17/16; E21B 47/01; E21B 49/08; E21B 49/10; E21B 49/00; E21B 49/081; G01N 1/12; G01N 2001/2071
(Continued)

(56) References Cited

U.S. PATENT DOCUMENTS

| 4,573,532 A | 3/1986 | Blake |
|---|---|---|
| 5,139,085 A | 8/1992 | Duvallet |

(Continued)

FOREIGN PATENT DOCUMENTS

| EP | 0526177 A1 | 2/1993 |
| WO | WO2007146801 A2 | 12/2007 |

OTHER PUBLICATIONS

International Application No. PCT/US2010/024843 Search Report and Written Opinion dated Oct. 4, 2010.

*Primary Examiner* — Daniel P Stephenson
(74) *Attorney, Agent, or Firm* — Haynes and Boone LLP

(57) ABSTRACT

A method and apparatus according to which a sample bottle drill collar section is assembled. In an exemplary embodiment, the apparatus includes a drill collar that includes an outer surface; a pocket accessible through an aperture in the outer surface, the pocket defining a first side wall and a second side wall; a bottle assembly disposed within the pocket, the bottle assembly comprising a sample bottle having an axial length; one or more clamps coupled to the outer surface and abutting or overlapping the bottle assembly, the one or more clamps at least partially retaining the bottle assembly in the pocket; and one or more spacers disposed within the pocket, the one or more spacers abutting the bottle assembly and at least one of the first and second side walls of the pocket.

27 Claims, 21 Drawing Sheets

(51) Int. Cl.
*E21B 49/08* (2006.01)
*E21B 49/10* (2006.01)
*G01N 1/12* (2006.01)
*G01N 1/20* (2006.01)

(52) U.S. Cl.
CPC ............... *E21B 49/10* (2013.01); *G01N 1/12* (2013.01); *G01N 2001/2071* (2013.01)

(58) Field of Classification Search
USPC ............... 166/264, 250.01, 162; 175/320, 58
See application file for complete search history.

(56) References Cited

U.S. PATENT DOCUMENTS

| | | |
|---|---|---|
| 6,745,835 B2 | 6/2004 | Fields |
| 7,367,394 B2 | 5/2008 | Villareal et al. |
| 9,068,405 B2 * | 6/2015 | Sherrill ................ E21B 17/16 |
| 9,187,998 B2 * | 11/2015 | Sherrill ................ E21B 17/16 |
| 9,234,421 B2 * | 1/2016 | Sherrill ................ E21B 49/10 |
| 2005/0011644 A1 | 1/2005 | Krueger et al. |
| 2005/0039527 A1 | 2/2005 | Dhruva et al. |
| 2005/0109538 A1 | 5/2005 | Fisseler et al. |
| 2013/0014994 A1 | 1/2013 | Sherrill et al. |

* cited by examiner

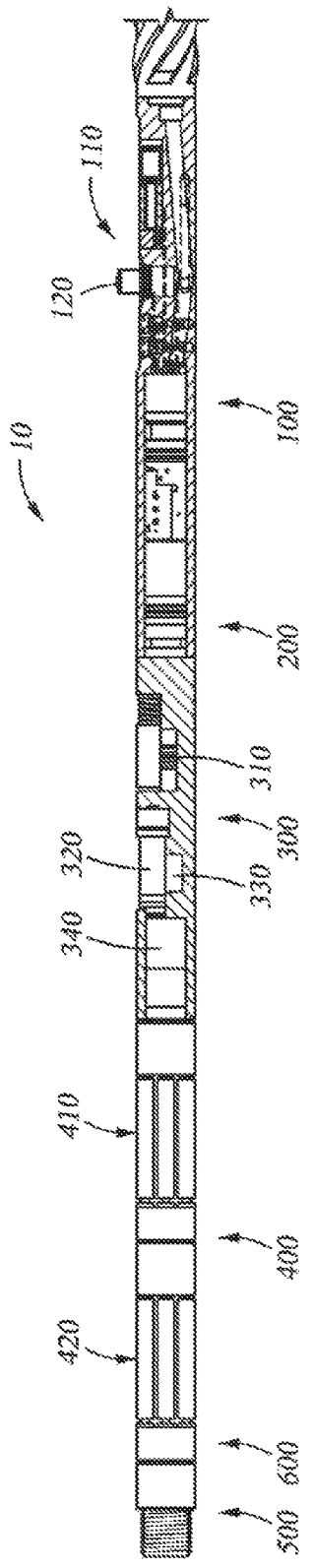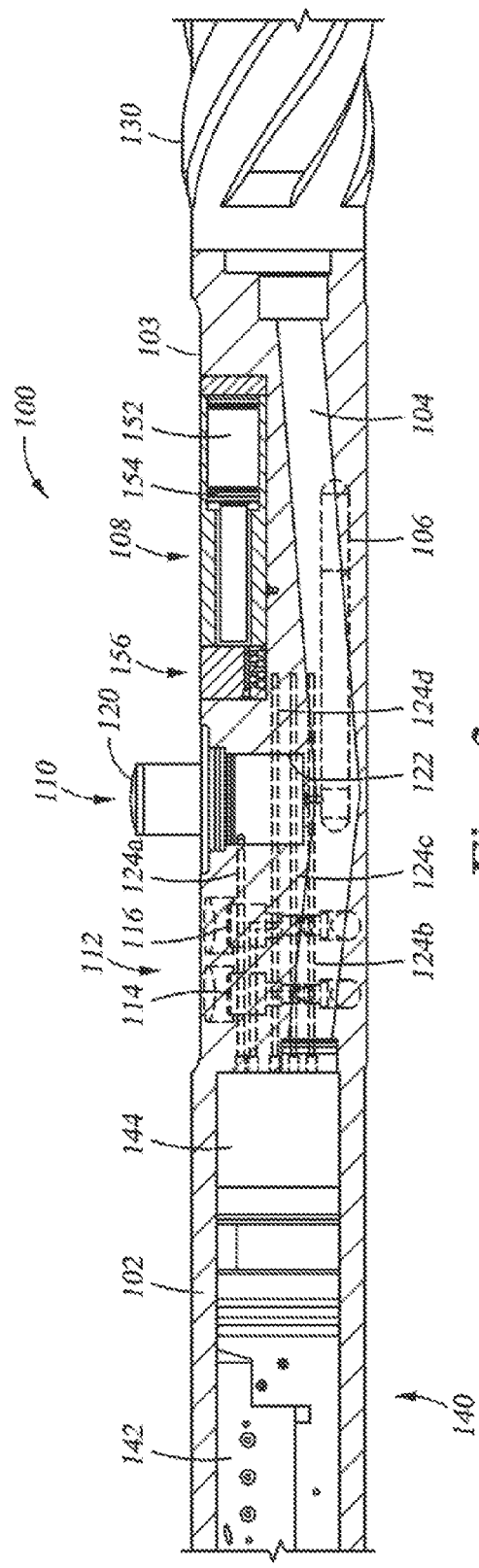
Fig. 2
Fig. 3

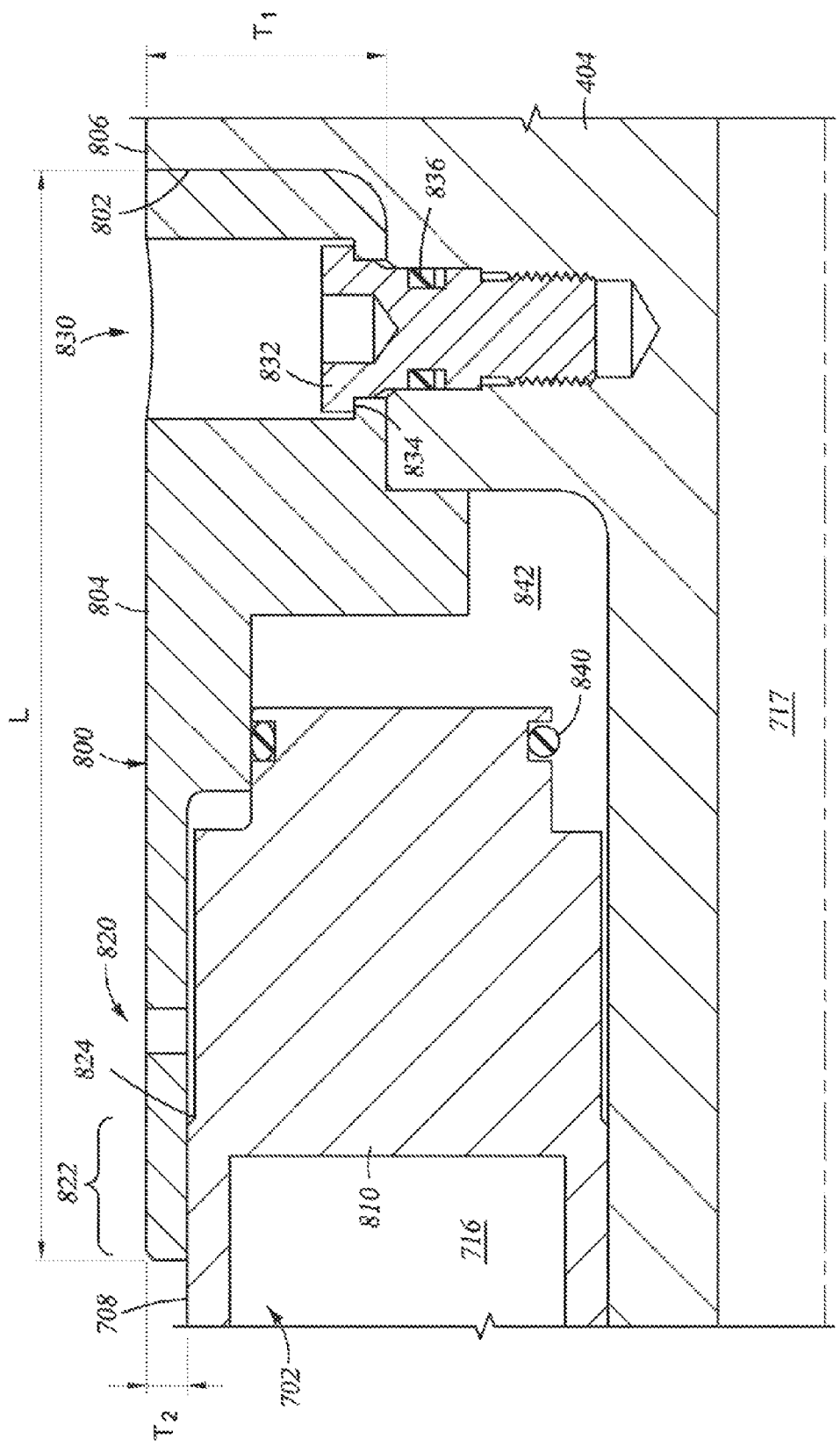

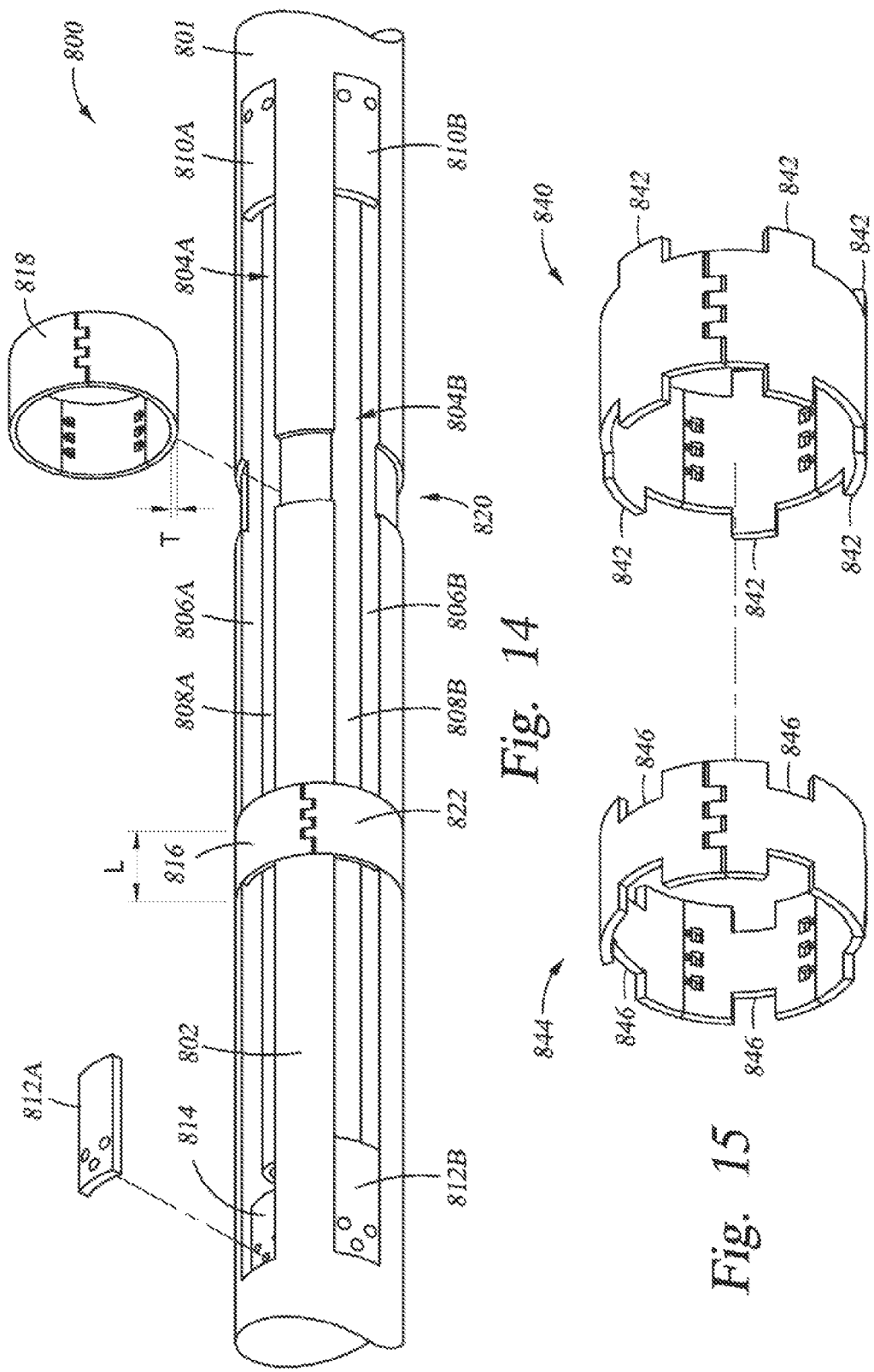

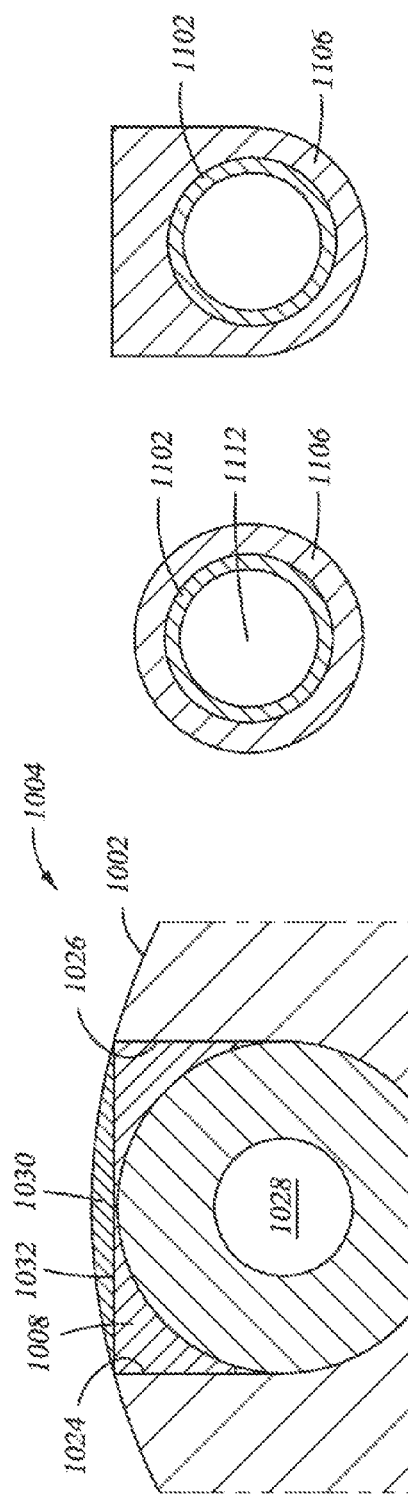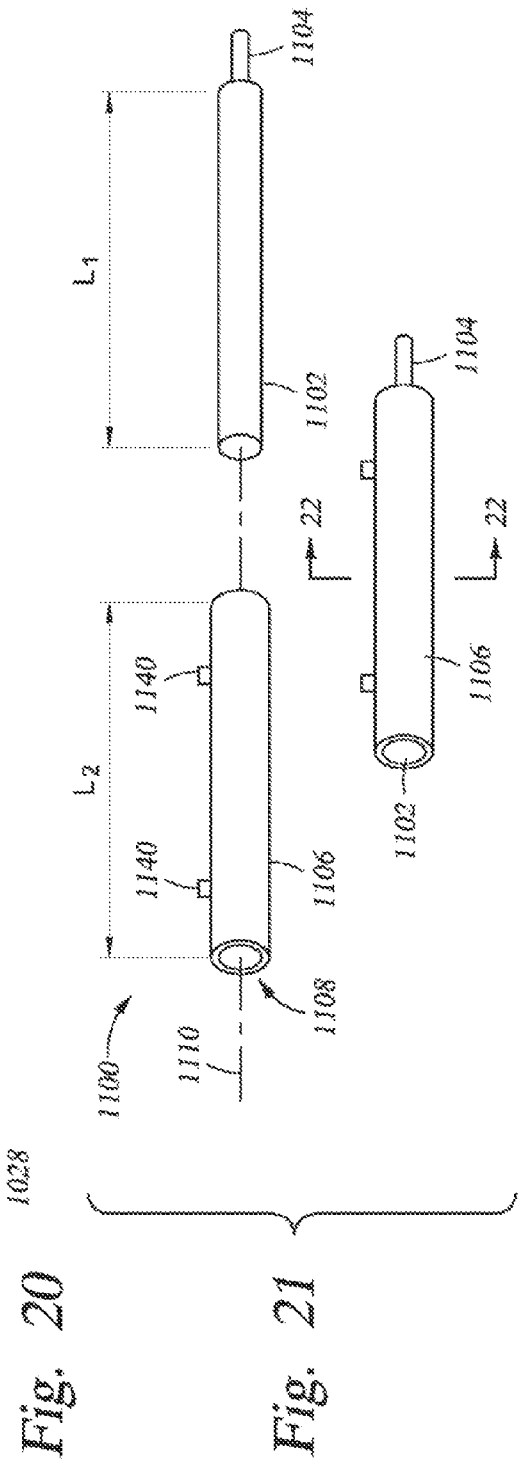

SYSTEMS AND METHODS OF A SAMPLE BOTTLE ASSEMBLY

CROSS-REFERENCE TO RELATED APPLICATIONS

This application is a continuation of U.S. patent application Ser. No. 13/580,104, filed Oct. 2, 2012, which is a United States National Stage Entry of International Patent Application No. PCT/US2010/024843, filed Feb. 20, 2010, the entire disclosures of which are hereby incorporated herein by reference.

BACKGROUND

During drilling and completion of hydrocarbon wells, ancillary operations are also performed, such as monitoring the operability of equipment used during the drilling process or evaluating the production capabilities of formations intersected by the wellbore. For example, after a well or well interval has been drilled, zones of interest are often tested to determine various formation properties such as permeability, fluid type, fluid quality, fluid density, formation temperature, formation pressure, bubble point, formation pressure gradient, mobility, filtrate viscosity, spherical mobility, coupled compressibility porosity, skin damage (which is an indication of how the mud filtrate has changed the permeability near the wellbore), and anisotropy (which is the ratio of the vertical and horizontal permeabilities). These tests are performed in order to determine whether commercial exploitation of the intersected formations is viable and how to optimize production.

Tools for evaluating formations and fluids in a well bore may take a variety of forms, and the tools may be deployed down hole in a variety of ways. For example, the evaluation tool may be a formation tester having an extendable sampling device, or probe, and pressure sensors, or the tool may be a fluid identification (ID) tool. The evaluation tool may also include sensors and assemblies for taking nuclear measurements. The evaluation tool may further include assemblies or devices which operate based on hydraulic power. For example, the tool may include an extendable density pad, an extendable coring tool, or an extendable reamer.

Often times an evaluation tool is coupled to a tubular, such as a drill collar, and connected to a drill string used in drilling the borehole. Thus, evaluation and identification of formations and fluids can be achieved during drilling operations. Such tools are sometimes referred to as measurement while drilling (MWD) or logging while drilling (LWD) tools. As previously suggested, the tool may include any combination of a formation tester, a fluid ID device, a hydraulically powered device, or any number of other MWD devices. As these tools continue to be developed, the functionality, size and complexity of these tools continue to increase. Consequently, multiple tools having different devices and functions may be placed in multiple drill collars. For example, as many as four or more drill collars extending over 40 feet may be used. The desire to use multiple tools or systems spread over multiple tubular sections in a drilling environment while maintaining the connectability and interchangeability of the tools, as well as the many electrical and fluid connections between the tools, is pushing the limits of current downhole evaluation and identification tools. Any advance which eases the assembly or disassembly of such tools, and/or any advance which makes the tools more resilient and less likely to be damaged during operations down hole, would provide a competitive advantage.

BRIEF DESCRIPTION OF THE DRAWINGS

For a detailed description of exemplary embodiments, reference will now be made to the accompanying drawings in which:

FIG. 2 shows a cross-sectional view of a measuring-while-drilling tool in accordance with at least some embodiments;

FIG. 3 shows a cross-sectional view of a probe collar section in accordance with at least some embodiments;

FIG. 13 shows a cross-sectional view of a sample bottle collar section proximate to another end-clap in accordance with at least some embodiments;

FIG. 14 shows a perspective view of a sample bottle collar section, with one intermediate clamp removed, in accordance with at least some embodiments;

FIG. 15 shows perspective view of alternative embodiments of intermediate clamps;

FIG. 20 shows a cross-sectional view, taken substantially along lines 20-20 of FIG. 19, in accordance with at least some embodiments;

FIG. 21 shows a perspective exploded view, as well as a perspective view, of a sample bottle assembly in accordance with at least some embodiments;

FIG. 22 shows a cross-sectional view, taken substantially along lines 22-22 of FIG. 21, in accordance with at least some embodiments;

FIG. 23 shows a cross-sectional view of a sample bottle assembly in accordance with at least some embodiments;

NOTATION AND NOMENCLATURE

Certain terms are used throughout the following description and claims to refer to particular system components. As one skilled in the art will appreciate, oilfield service companies may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to up or down will be made for purposes of description with "up", "upper", "upwardly" or "upstream" meaning toward the surface of the well and with "down", "lower", "downwardly" or "downstream" meaning toward the terminal end of the well, regardless of the well bore orientation. In addition, in the discussion and claims that follow, it may be sometimes stated that certain components or elements are in fluid communication.

In addition, in the discussion and claims that follow, it may be sometimes stated that certain components or elements are in "fluid communication" and/or are "fluidly coupled". By this it is meant that the components are constructed and interrelated such that a fluid could be communicated between them, as via a passageway, tube, or conduit.

The designation "MWD" or "LWD" are used to mean all generic measurement while drilling or logging while drilling apparatus and systems.

"Axial length" shall mean the length of an object measured along a long or longitudinal axis defined by a drill collar to which the object couples.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Figure 1:
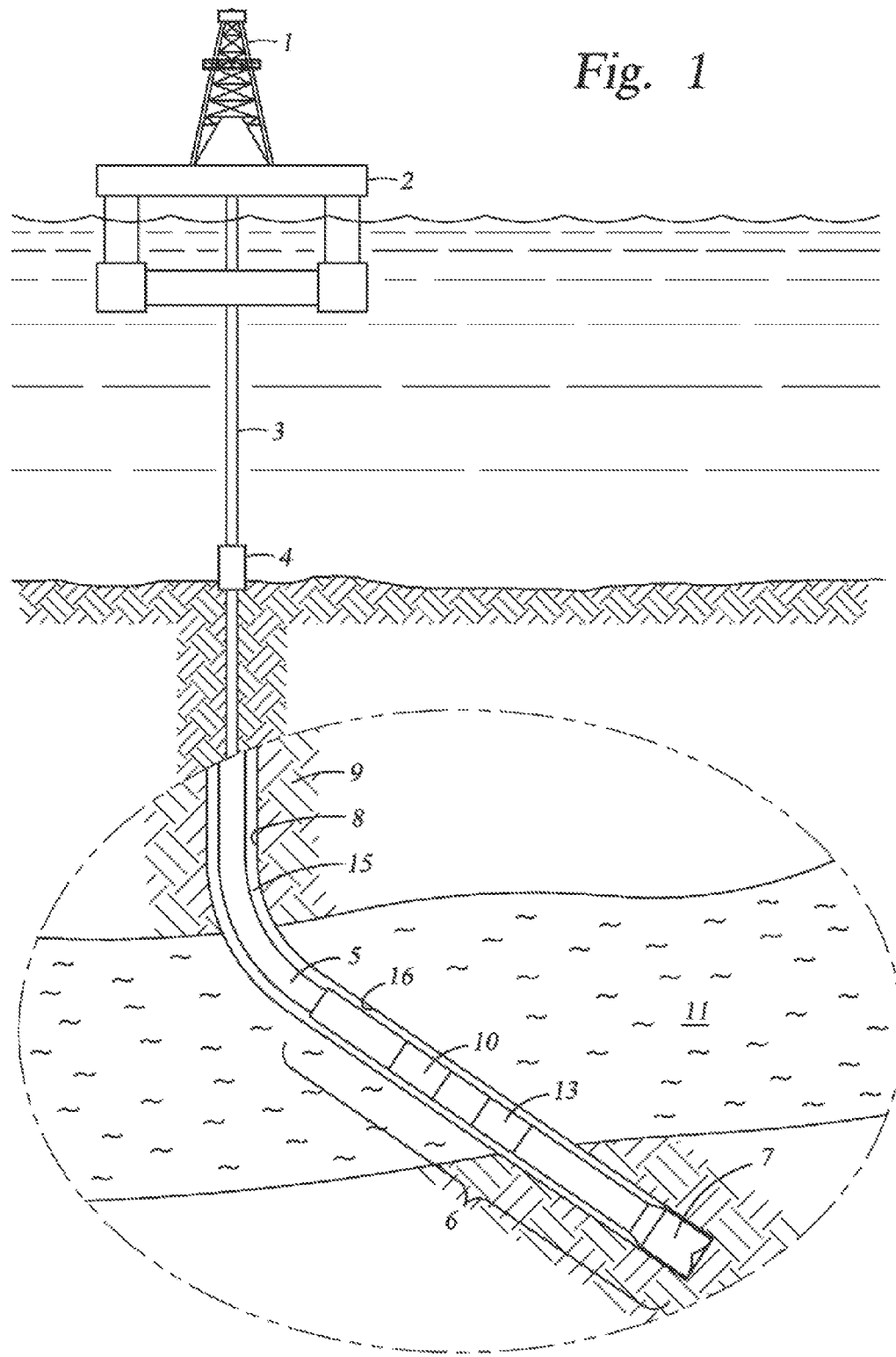
FIG. 1 shows a drilling system in accordance with at least some embodiments.

Referring initially to FIG. 1, a MWD formation evaluation or formation fluid identification tool 10 is shown schematically as a part of bottom hole assembly 6 which includes an MWD sub 13 and a drill bit 7 at the distal end. The bottom hole assembly 6 is lowered from a drilling platform 2, such as a ship or other drilling platform, via a drill string 5. The drill string 5 extends through a riser 3 and a well head 4. Drilling equipment is supported within and around derrick 1 and rotates the drill string 5 and the drill bit 7, causing the bit 7 to form a borehole 8 through the formation material 9. The volume defined between the drill string 5 and the borehole 8 is referred to as the annulus 15. The borehole 8 penetrates subterranean zones or reservoirs, such as reservoir 11, that are believed to contain hydrocarbons in a commercially viable quantity. It is also consistent with the teachings herein that the MWD tool 10 is employed in other bottom hole assemblies and with other drilling apparatus in land-based drilling with land-based platforms, as well as offshore drilling as shown in FIG. 1. In addition to the MWD tool 10, the bottom hole assembly 6 may also contain various other systems, such as a down hole drill motor, a rotary steerable tool, a mud pulse telemetry system, and other MWD or LWD sensors and systems.

Figure 1B:
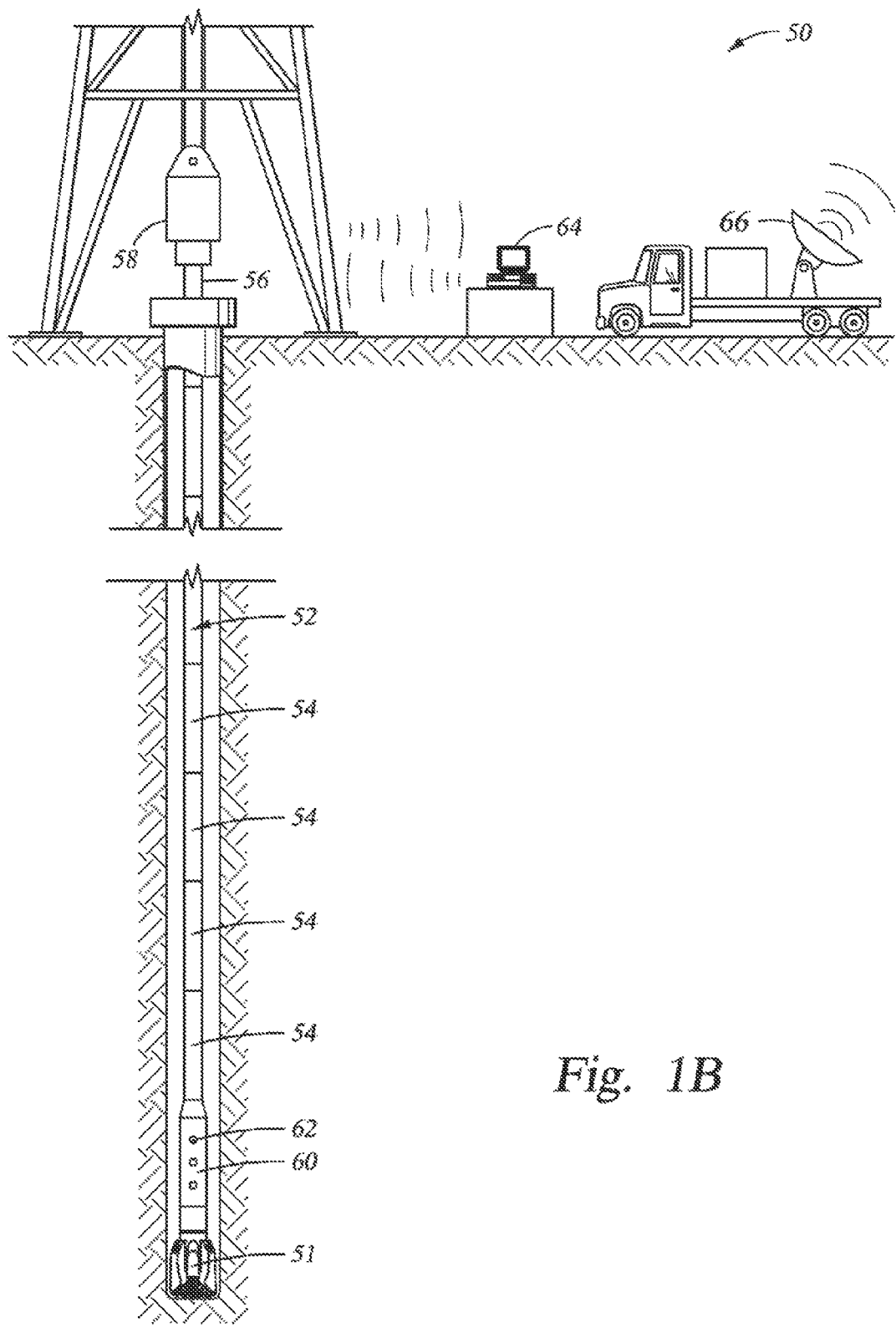
FIG. 1B shows a drilling system in accordance with at least some embodiments.
Figure 1C:
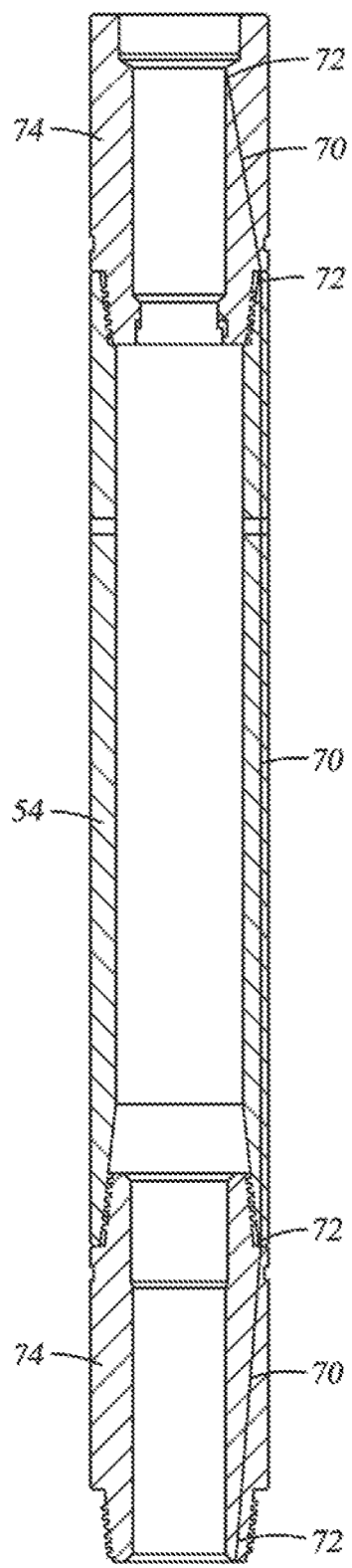
FIG. 1C shows a wired drill collar section in accordance with at least some embodiments.

In some embodiments, the tool and bottom hole assembly may be part of a telemetry and/or electromagnetic network 50 with wired pipes, as shown in FIG. 1B. In particular, in the embodiments of FIG. 1B formation testing or survey equipment 60, just above a drill bit 51, is coupled to a drill string 52 formed by a series of wired drill pipes 54 connected for communication across junctions using communication elements as described below. It will be appreciated that drill string 52 can be other forms of conveyance, such as coiled tubing or wired coiled tubing. Other components of the network 50 comprise a Kelly 56, a top-hole repeater unit 58 to interface the network 50 with drilling control operations and with the rest of the world, a computer 64 in the rig control center to act as a server, and an uplink 66. The testing tool 60 with sensors 62 is linked into the network 50 for communication along conductor pathways and along the wired drill string 52. As shown in FIG. 1C, a pipe section 54 of the wired drill string 52 includes conductors 70 that traverse the entire length of the pipe section. Communication elements 72 allow the transfer of power and/or data between the pipe section 54 and other pipe components 74 such as subs, couplers and other pipes. A data/power signal may be transmitted along the pipe from one end of the tool through the conductor(s) 70 to the other end across the communication elements 72.

FIG. 2 shows an exemplary embodiment of the MWD tool 10. A first end of the tool 10 includes a probe drill collar section 100. For reference purposes, the first end of the tool 10 at the probe collar section 100 is in some embodiments the lowermost end of the tool, which is closest to the distal end of the bottom hole assembly 6. The probe collar section 100 comprises a formation tester or formation probe assembly 110 having an extendable sample device or extendable probe 120. The tool 10 also comprises a power drill collar section 300 coupled to the probe collar section 100 via an interconnect assembly 200. As will be described more thoroughly below, the interconnect assembly 200 comprises fluid and power/electrical pass-through capabilities such that the various connections in the interconnect assembly are able to communicate, for example, electrical signals, power, formation fluids, hydraulic fluids and drilling fluids to and from the probe collar 100 and the power collar 300.

Power collar 300 comprises certain components such as a flush pump assembly 310, a flow gear or turbine assembly 320, an electronics module 330 and a drilling fluid flow bore diverter 340. Coupled to the power collar 300 is another drill collar section called the sample bottle drill collar section 400. The sample bottle drill collar 400 may include one or more sample bottle assemblies 410, 420. Coupled to the sample bottle drill collar 400 is a terminator drill collar section 500. In some embodiments the coupling between the sample bottle drill collar 400 and the terminator drill collar 500 comprises another interconnect assembly—interconnect assembly 600.

FIG. 3 shows, in greater detail, an embodiment of the of the probe collar section 100. A drill collar 102 houses the formation tester or probe assembly 110. The probe assembly 110 comprises various components for operation of the probe assembly 110 to receive and analyze formation fluids from the earth formation 9 (FIG. 1) and the reservoir 11 (FIG. 1). The probe member 120 is disposed in an aperture 122 in the drill collar 102 and extendable beyond the drill collar 102 outer surface, with FIG. 3 showing the extended orientation. The probe member 120 is also retractable to a position recessed beneath the drill collar 102 outer surface. In some embodiments the probe assembly 110 comprises a recessed outer portion 103 of the drill collar 102 outer surface adjacent the probe member 120. The probe assembly 110 comprises a draw down piston assembly 108, a sensor 106, a valve assembly 112 having a flow line shutoff valve 114 and equalizer valve 116, and a drilling fluid flow bore 104. At one end of the probe collar 100, in some embodiments the lower end when the tool 10 is disposed in the borehole 8, is an optional stabilizer 130, and at the other end is an assembly 140 that comprises a hydraulic system 142 and a manifold 144.

The draw down piston assembly 108 includes a piston chamber 152 containing a draw down piston 154 and a manifold 156 including various fluid and electrical conduits and control devices. The draw down piston assembly 108, the probe 120, the sensor 106 (e.g., a pressure gauge) and the valve assembly 112 communicate with each other and various other components of the probe collar section 100, such as the manifold 144 and hydraulic system 142, and the tool 10 via conduits 124*a*, 124*b*, 124*c* and 124*d*.

Still referring to FIG. 3, the conduits 124*a*, 124*b*, 124*c*, 124*d* include various fluid flow lines and electrical conduits for operation of the probe assembly 110 and probe collar 100. For example, one of conduits 124 provides a hydraulic fluid to the probe 120 to extend the probe 120 and engage the formation 9. Another of these conduits 124 provides hydraulic fluid to the draw down piston 154, actuating the piston 154 thus causing reduced pressure to draw fluid into the probe 120. Another of the conduits 124 is a formation fluid flow line communicating formation fluid to the sensor 106 for measurement, and to the valve assembly 112 and the manifold 144. The flow line shutoff valve 114 controls fluid flow through the flow line, and the equalizer valve 116 is actuatable to expose the flow line and probe assembly 110 to a fluid pressure in an annulus surrounding the probe collar 100, thereby equalizing the pressure between the annulus and the probe assembly 110. The manifold 144 receives the various conduits 124*a*, 124*b*, 124*c*, 124*d*, and the hydraulic system 142 directs hydraulic fluid to the various components of the probe assembly 110 as just described. One or more of the conduits 124 carry one or more electrical conductors for communicating power from a power source, and also for communicating control signals from a controller in the tool or from a controller at the surface of the well.

Drilling fluid flow bore 104 may be offset or deviated from a longitudinal axis of the drill collar 102, as shown in FIG. 3, such that at least a portion of the flow bore 104 is not central in the particular portion of the drill collar 102 and not parallel to the longitudinal axis. The deviated portion of the flow bore 104 allows the receiving aperture 122 to be placed in the drill collar 102 such that the probe member 120 can be fully recessed below the drill collar 102 outer surface. As shown in FIG. 3, space for formation testing and other components is limited. Drilling fluid passes through the probe collar 100 to reach the drill bit 7 (FIG. 1). The deviated or offset flow bore 104 allows an extendable sample device such as probe 120 and other probe embodiments described herein to retract and be protected as needed, and also to extend and engage the formation for formation testing.

Figure 4:
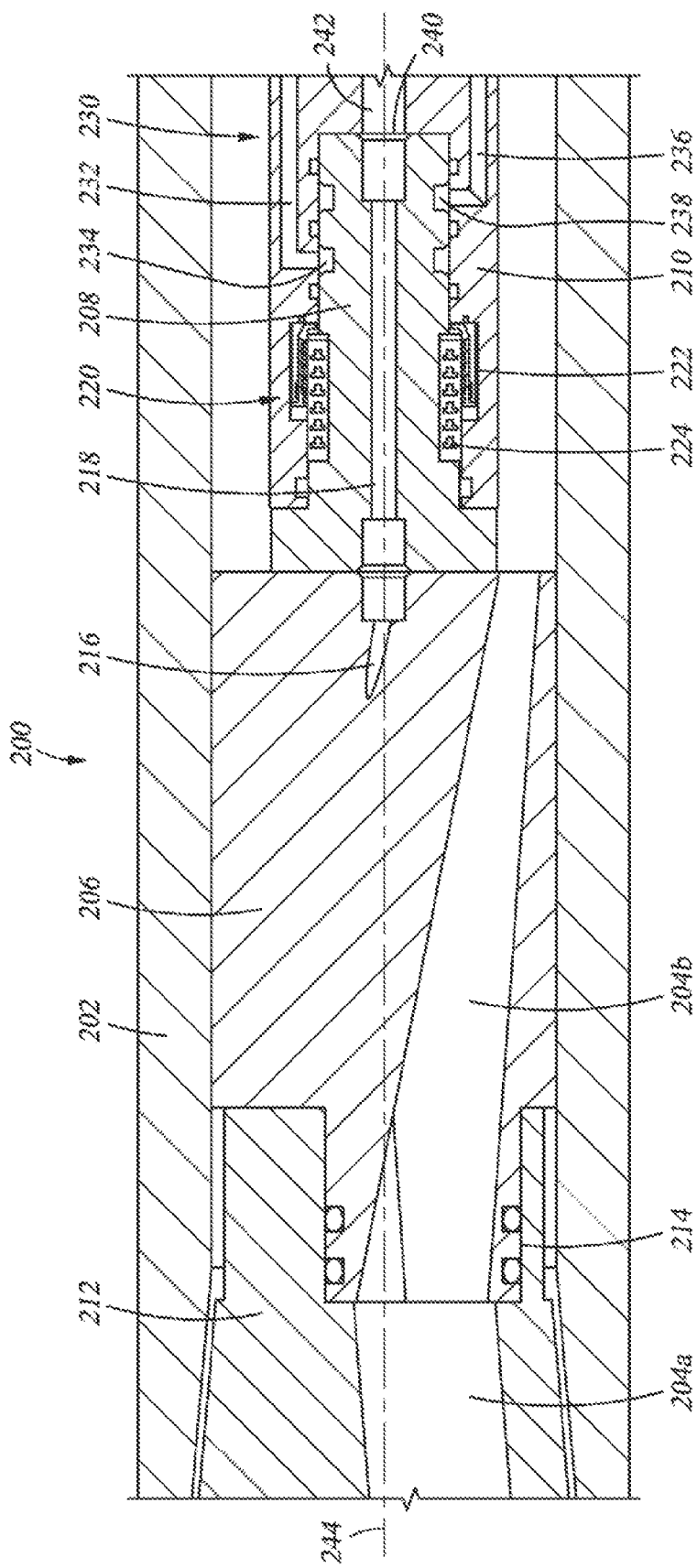
FIG. 4 shows a cross-sectional view of an interconnect assembly in accordance with at least some embodiments.

FIG. 4 shows a cross-sectional view of an embodiment of the interconnect assembly 200 in greater detail. A drill collar 202 couples to the drill collar 102 of the probe collar section 100 of FIG. 3. The interconnect assembly 200 further comprises a manifold 206, a manifold extension or connector 208, a manifold receiving portion or connector 210 and a flow bore housing 212. The flow bore housing 212 is connected to the manifold 206, and a flow bore 204*a* of the flow bore housing 212 communicates with a flow bore 204*b* in the manifold 206. In one embodiment, the flow bore housing 212 may be disconnected from the manifold 206 at the connection 214. The flow bore 204*b* connects to a flow bore (not shown) adjacent the manifold extension 208 and manifold receiving portion 210.

The manifold 206 further comprises a flow port 216 connected to a flow line 218 in the manifold extension 208. The manifold extension 208 comprises a first electrical connector housing 224 having one or more electrical connectors. The manifold receiving portion 210, which receives and couples to the manifold extension 208, includes a second electrical connector housing 222 having one or more electrical connectors that couple to and communicate with the electrical connector or connectors of the first electrical connector housing 224. In this configuration, as shown in FIG. 4, the electrical connector housings 222, 224 provide an electrical connection 220 wherein one or more electrical conduits or lines (not shown) in the receiving portion 210 communicate with one or more electrical conduits or lines (not shown) in the manifold 206. The electrical conduits may carry electrical data signals or power, for example.

The manifold extension 208 further comprises a first port 234 communicating with a first fluid flow line 232 in the receiving portion 210, and a second port 238 communicating with a second fluid flow line 236 in the receiving portion 210. The manifold extension fluid flow line 218 couples to a receiving portion fluid flow line 242 at connection 240. In the configuration shown in FIG. 4, the fluid flow lines and ports just described combine to provide a fluid line connection 230. The ports 234, 238 connect to fluid conduits or lines (not shown) in the manifold 206. The fluid flow lines 232, 236, 242 connect to fluid conduits or lines (not shown) in the hydraulic assembly 140 of the drill collar section 100. In one embodiment, the fluid flow line 232 carries hydraulic system fluid, the fluid flow line 238 carries a hydraulic reservoir fluid and the fluid flow line 242 (and the fluid line 218) carries a formation fluid drawn through the probe 120 (FIG. 3).

In one embodiment, the electrical connection 220 and the fluid line connection 230 extend radially about the manifold extension 208 a full 360 degrees. For example, the electrical connector housings 222, 224 are concentric cylinders such that they extend completely around the manifold extension 208. The ports 234, 238 may extend completely around the manifold extension 208 also. Thus, in any radial position of the manifold extension 208 about a longitudinal axis 244, the electrical connector housings 222, 224 will be in contact and communicating, and the ports 234, 238 will be communicating with the fluid flow lines 232, 236, respectively. One or both of the manifold extension 208 and the receiving portion 210 may rotate relative to the other, and the electrical connection 220 and the fluid line connection 230 will not be disturbed. The rotatable nature of the connections 220, 230 and the relationship between the manifold extension 208 and the receiving portion 210 provide a rotatable interconnect assembly 200.

In one embodiment, the interconnect assembly is disconnectable. The manifold 206 and manifold extension 208 are removable from the receiving portion 210. The manifold 206 and manifold extension 208 are axially displaced and the receiving portion 210 releases the manifold extension 208. Thus, any drill collar sections or tools coupled above and below the interconnect assembly 200 are removable from one another. The interconnect assembly 200 of FIG. 4 is merely illustrative, and other interconnect assemblies may be equivalently used.

Figure 5:
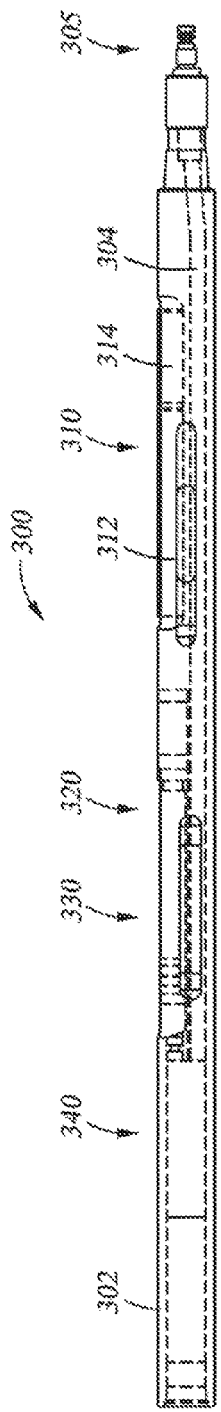
FIG. 5 shows a side elevation view of a power drill collar section in accordance with at least some embodiments.

FIG. 5 shows a side elevation view of the power drill collar section 300 in greater detail. In particular, the power collar 300 comprises a drill collar 302, a flush pump assembly 310 having a flush pump 312 and external reservoir 314, a flow gear or turbine assembly 320, an electronics module 330 and a drilling fluid flow bore diverter 340. At one end of the power collar 300 is a connector 305 for connection to corresponding components of an interconnect assembly, such as interconnect assembly 200. For example, the connector 305 may correspond with the housing 212, manifold 206 and manifold extension 208 of FIG. 4. The connector 305 enables electrical signals, power and fluids to pass through connections therein to/from a drill collar section or MWD tool below. The connector 305 enables the power collar 300 to be removable from the probe collar 100, for example, or other MWD tool to which the power collar 300 may be connected.

Figure 6:
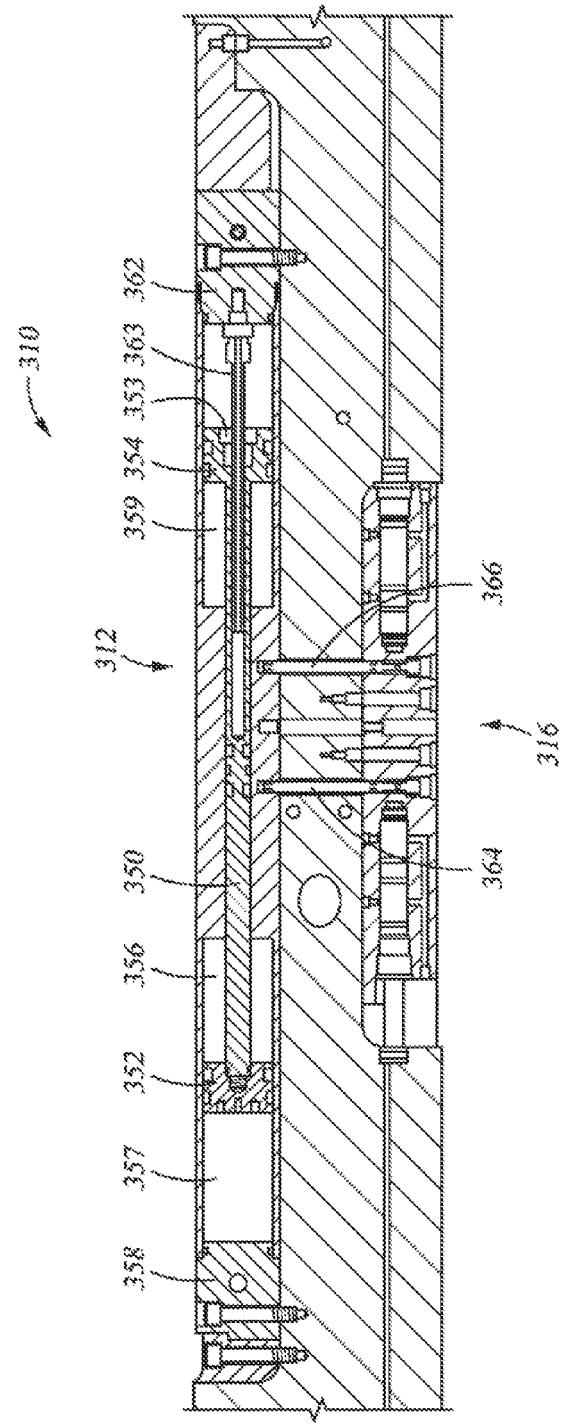
FIG. 6 shows a cross-sectional view of a flush pump assembly in accordance with at least some embodiments.

FIG. 6 shows a cross-section view of the flush pump assembly 310. In particular, the piston 350 reciprocates in the cylinder 356 between the ends 358, 362. The end 362 includes a hydraulic fluid extension 363 inserted into a receptacle 353 in the piston end 354. Hydraulic fluid flows into and out of the piston extension 363 to adjust hydraulic fluid pressure in the receptacle 353. The adjustable hydraulic fluid pressure causes the piston 350 to reciprocate, in turn causing the piston end 352 to reciprocate in a chamber 357 and the piston end 354 to reciprocate in a chamber 359. The dual pistons ends 352, 354 in the dual chambers 357, 359 provide a dual action pump 312, wherein multiple fluid flow paths may be established in the fluid flow lines 364, 366 and other fluid flow lines shown as part of the fluid manifold and control valve assembly 316. Check valves in the assembly 316 control the direction of the fluid flows in the various flow lines. The various embodiments are not limited to the pump embodiment of FIG. 6, as other pumps and dual action pumps may be equivalently used as the flush pump assembly 310.

Figure 7:
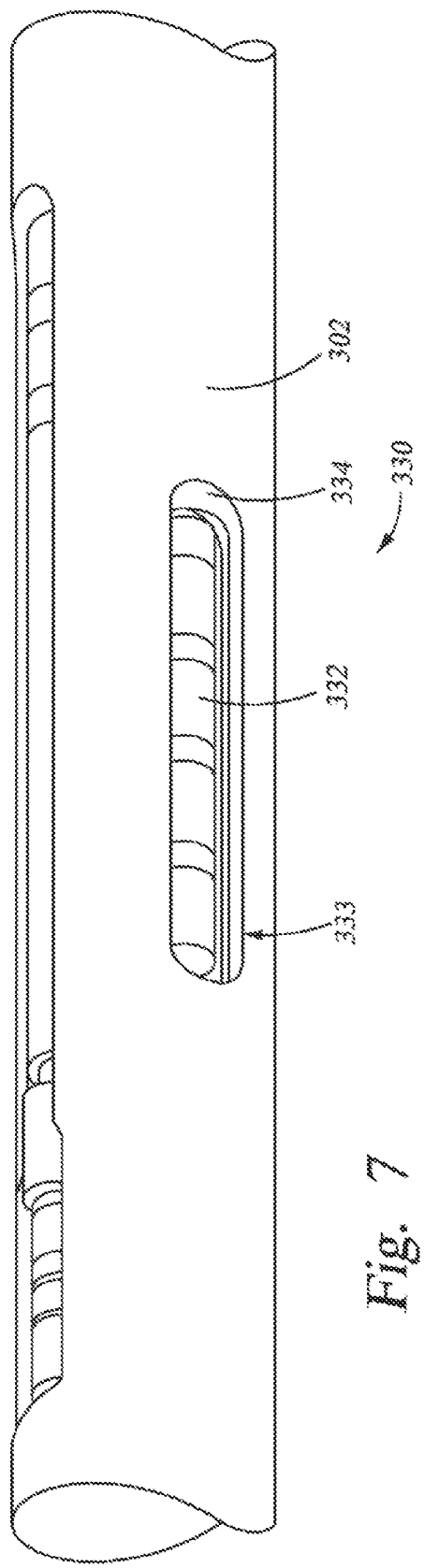
FIG. 7 shows a perspective view of an electronics module in accordance with at least some embodiments.

FIG. 7 shows a perspective view of electronics module 330 in greater detail. In particular, the module 330 includes an outsert 332 mounted through an aperture 333 and into a pocket 334 in the drill collar 302. The outsert 332 is removable from the exterior of the drill collar, and the pocket 334 can easily receive other outserts, making the outserts easily interchangeable in the event of an electronics failure. The electronics in the electronics module 330 control various components and operations of the tool, receive information from the tool, and operate the tool.

Figure 8:
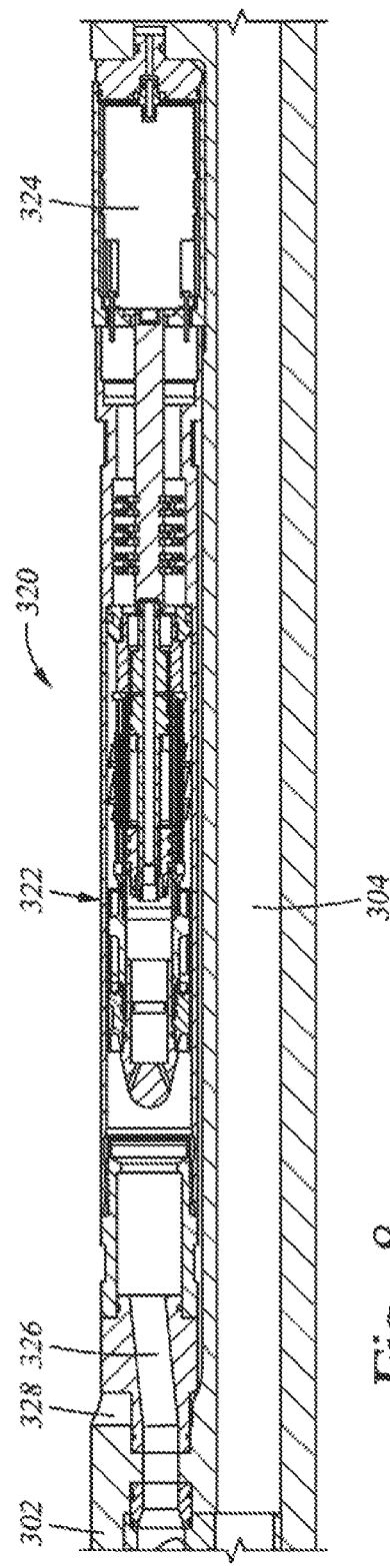
FIG. 8 shows a cross-sectional view of a flow gear or turbine assembly in accordance with at least some embodiments.

FIG. 8 shows a cross-sectional view the flow gear or turbine assembly 320 is shown in greater detail. In particular, the turbine assembly 320 comprises flow gear 322 coupled to a hydraulic pump 324. A diversion flow bore 326 communicates fluid to the flow gear 322. The flow gear 322, the hydraulic pump 324 and the flow bore 326 may be offset from the primary flow bore 304, such as in a pocket 328.

Figure 9:
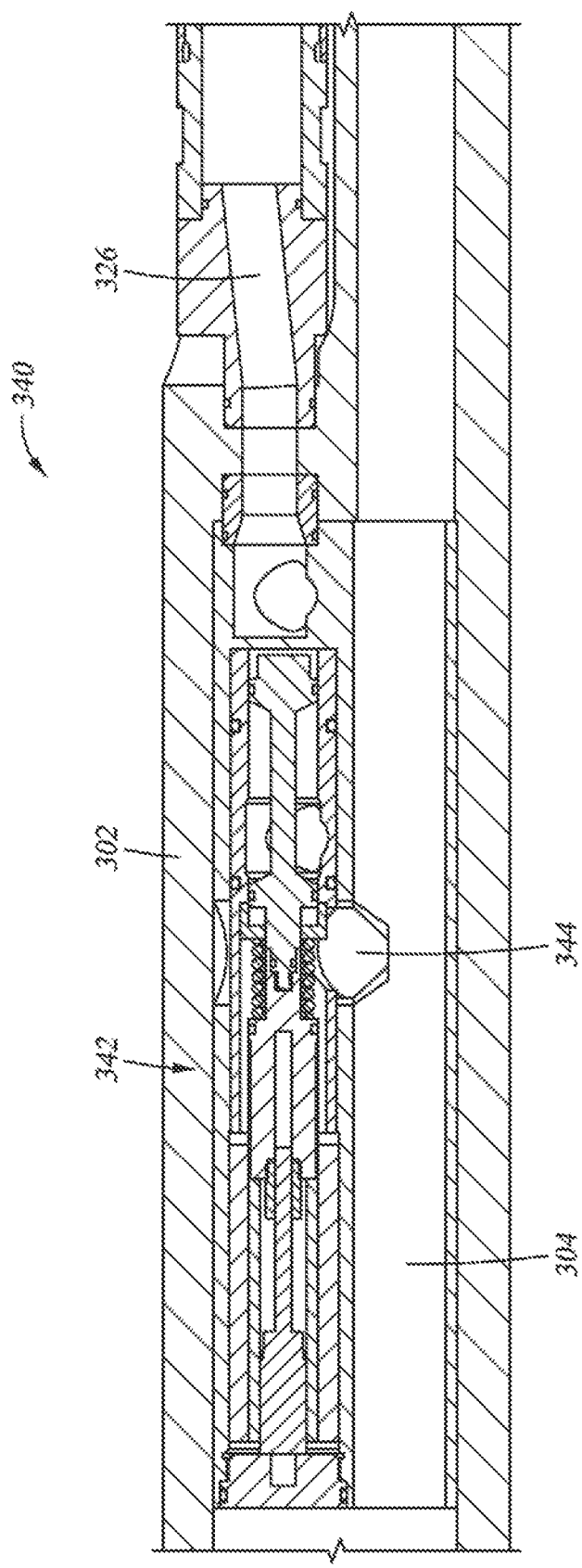
FIG. 9 shows a cross-sectional view of a drilling fluid flow bore diverter in accordance with at least some embodiments.

FIG. 9 shows the drilling fluid flow bore diverter 340 in greater detail. In particular, the diverter 340 includes a valve assembly 342 and a flow port 344. When valve assembly 342 is opened, drilling fluid from the primary flow bore 304 is diverted through the flow port 344, through the valve assembly 342, and into the diversion flow bore 326. The flow bore 326 fluidly communicates with the flow gear 322 (FIG. 8), thereby providing the diverted drilling fluid to the flow gear 322. The diverted drilling fluid causes the flow gear 322 to turn, thereby operating the hydraulic pump 324. The hydraulic pump 324 provides hydraulic power to other portions of the tool (e.g., to extend and retract the probe 120 (FIG. 2)). Thus, selective actuation of the valve assembly 342 selectively provides the drilling fluid that drives the power generating flow gear 322 and hydraulic pump 324. Further, the valve assembly 342 may be adjusted to allow varying amounts of drilling fluid flow through the valve assembly 342, thereby providing variable power generation from the flow gear 322 and the hydraulic pump 324.

Figure 10:
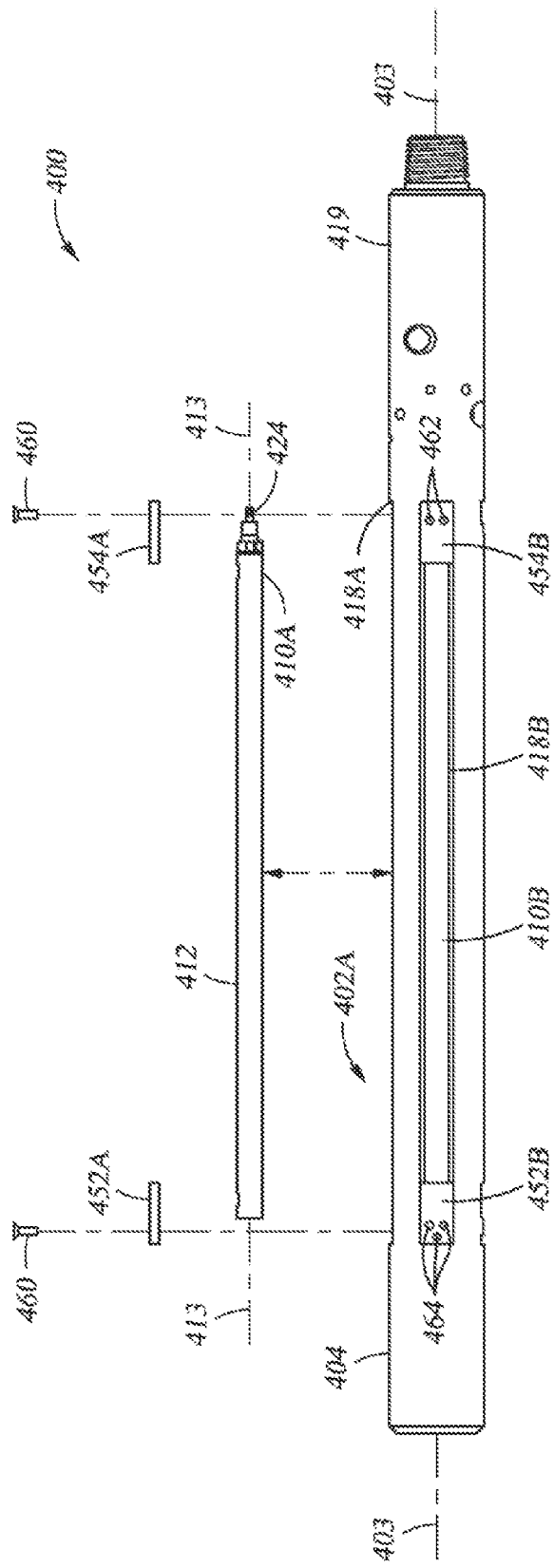
FIG. 10 shows a side elevation, partial exploded, view of a sample bottle collar section in accordance with at least some embodiments.

In some circumstances, it may be desirable to collect a sample of the fluids within a reservoir 11 and bring the sample to the surface for analysis. The sample bottle drill collar section 400, in combination with the other components, provides the functionality for storing formation fluids and bringing the fluids to the surface. FIG. 10 shows a side perspective view of a sample bottle drill collar section 400 in accordance with at least some embodiments. In particular, the sample bottle drill collar section 400 comprises a drill collar 404 housing at least one sample bottle assembly 410. In the configuration of FIG. 10, the drill collar 404 houses four sample bottle assemblies 410, but greater or fewer sample bottle assemblies may be housed as a function of the diameter of the drill collar 404. Each sample bottle assembly 410 includes a bottle section 412 along with a connector 424 for fluidly coupling the bottle section 412 to the other down hole devices. Each sample bottle assembly 410 is inserted into a cavity or pocket 402 in the drill collar 404, the pocket 402 accessible through an aperture 418 in the outer surface 419 of the drill collar 404. Sample bottle assembly 410A is shown suspended above its pocket 402A, while sample bottle assembly 410B is shown installed within its pocket 402B, to illustrate that the sample bottle assemblies may be selectively installed and removed from the sample bottle drill collar section 400. As shown, the drill collar 404 defines a central axis 403 along the long dimension of the collar 404. Likewise, each sample bottle assembly 410 defines a central axis 413 along the long of the sample bottle assembly. When the sample bottle assembly 410 is coupled within a pocket of the drill collar 404, the central axis 413 of the sample bottle assembly 410 is parallel to the central axis 403 of the drill collar 404.

Figure 11:
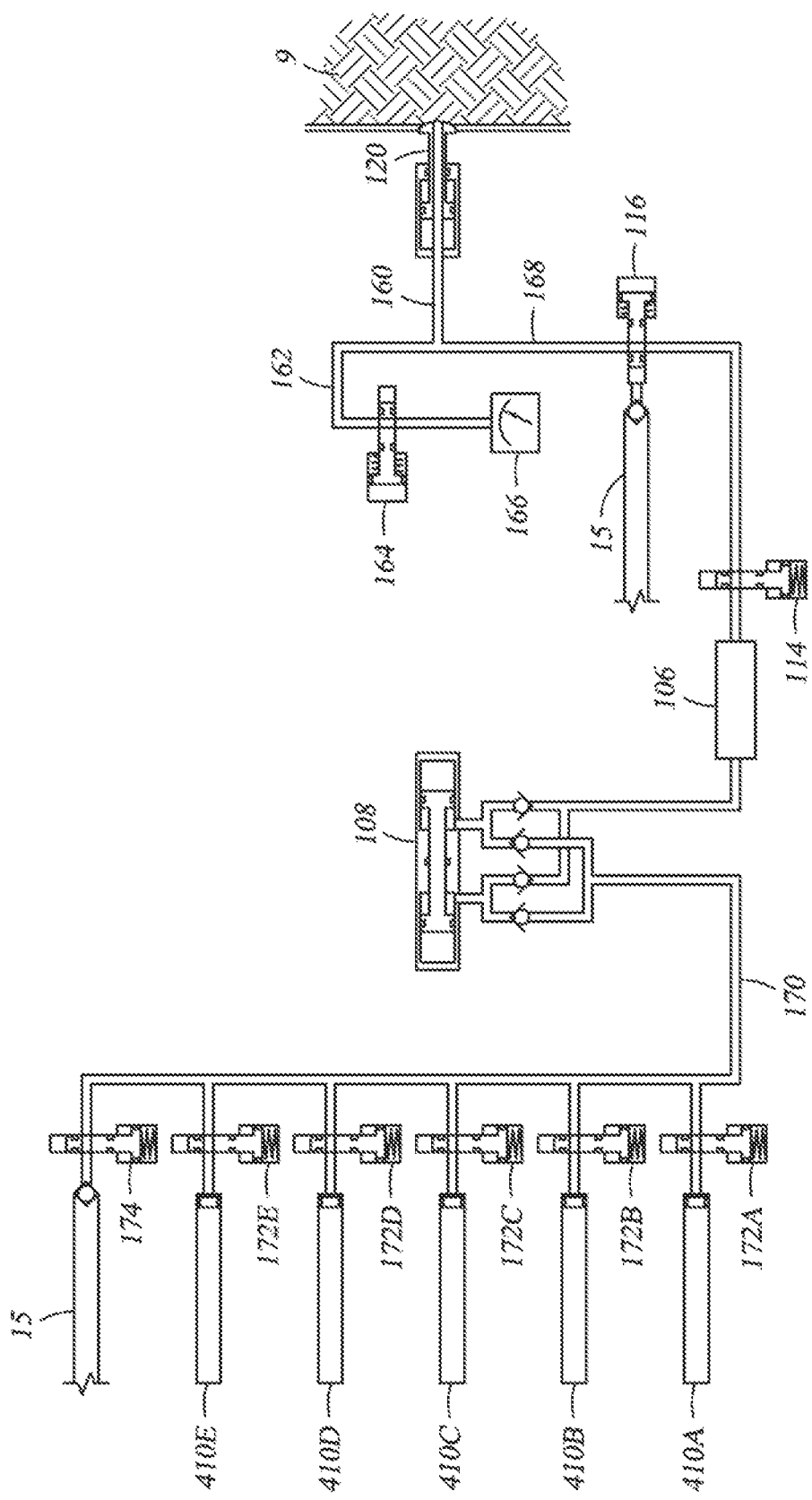
FIG. 11 shows a schematic of a sample collection system in accordance with at least some embodiments.

FIG. 11 shows, schematically, a sample probe to sample bottle assembly system in accordance with at least some embodiments. The various components illustrated span several drill collar sections (e.g., the sample bottle assemblies on the left of the figure reside within the sample bottle drill collar section 400, while the probe on the right resides within the probe collar section 110); however, the components are shown together as a single integrated system so as not to unduly complicate the figure. In particular, the system comprises a sample probe 120 fluidly coupled to a flow line 160. Flow line 160 couples to a test branch 162 comprising valve 164 and meter 166, and flow line 160 also couples to a flow branch 168. Each flow branch will be discussed in turn.

Flow line 162 couples to shut-in valve 164 and meter 166. When shut-in valve 164 is closed, the meter 166 is fluidly isolated from the probe 120. However, when shut-in valve 164 is opened, the meter 166 is fluidly coupled to the probe 120 such that any suitable measurement can be made. For example, in some embodiments the meter 120 is a pressure meter, which thus measures the pressure of the formation fluid to which the probe 120 is fluidly coupled. Such measurements can be made both when the pump 108 (discussed below) is operational, and when pump 108 is fluidly isolated from the probe 120.

Still referring to FIG. 11, flow line 168 couples to a plurality of components, including equalizing valve 116, flow line shut-off valve 114, sensor 106, draw-down pump 108 and flow line 170. When desired to equalize the pressure in the probe 120 to that of the borehole, shut off valve 114 is closed and equalizing valve 116 is opened, thus equalizing the pressure to that of annulus 15. Flow line 170 fluidly couples, in turn, to a plurality of bottle valves 172, which bottle valves couple to a respective plurality of sample bottle assemblies 410. Flow line 170 also couples to vent valve 174. Vent valve 174 selectively vents flow line 170 to the annulus 15.

During periods of time when a formation draw-down test is being performed, equalizing valve 116 is closed, flow line shut off valve 114 is opened, pump 108 is operated to draw fluids, and vent valve 174 is open, thus creating a flow path through the system. Initially in the draw-down configuration, the various flow lines carry the fluid within the bore hole (e.g., drilling fluid), based in part on the fluids within the bore hole entering the probe when retracted, and/or drawing portions of those fluids that have penetrated or invaded the formation 9. Eventually, however, the fluids moving through the various flow lines will be almost exclusively formation fluids.

Various tests can be performed on the formation and the formation fluid associated with the draw down. For example, as the fluids flow through sensor 106, various parameters may be measured. Sensor 106 may be a resistivity sensor, a conductivity sensor, a density sensor, a dielectric sensor and/or a torroidal conductivity dielectric sensor. Moreover, during draw-down test valve 164 may be opened, and the pressure within the flow line read by sensor 166. Further still, with sensor 106 fluidly coupled to the probe 120 and fluids flowing, flow line shut off valve 114 may then be closed, and the amount of time the formation takes to return to an original static pressure may be determined.

Regardless of the precise number and nature of tests that may be performed with respect to the formation, in some cases samples of the fluid within the flow lines (and thus samples of the fluid in the bore hole and/or formation fluid) may be taken and stored. For example, valve 172A may be opened during a draw-down test, and vent valve 174 closed, thus forcing fluid into sample bottle 410A. Thereafter, valve 172A is closed and vent valve 174 is opened again. At a later time within the particular draw-down test, or perhaps a different draw-down test at a different depth in the bore hole, valve 172B is opened and vent valve 174 is closed, thus forcing fluid into sample bottle 410B. The sample bottles may be removed from the sample bottle drill collar section 400 at the surface, and the fluids therein analyzed in a laboratory.

The specification now turns to systems and related methods of attaching the sample bottle assemblies in the sample bottle drill collar section 400. Returning again to FIG. 10, in accordance with at least some embodiments each sample bottle assembly 410 is held within a pocket 402, at least in part, by an end-clamp 452 and an end-clamp 454. Sample bottle assembly 410A is shown suspended above its pocket 402A, along with its end-clamps 452A and 454A likewise suspended above the pockets, to illustrate how the sample bottle assembly 410A and end-clamps relate. Conversely, sample bottle assembly 410B is shown installed within pocket 402B with end-clamps 452B and 454B shown attached to the collar 404.

Each end-clamp is held in place by one or more fasteners. For example, end clamps 454, which couple to the end of the sample bottle assembly that comprises connector 424, may use two fasteners, as illustrated by the two apertures 462 in the end-clamp 454B. End-clamps 452, which couple to the end sample bottle assembly opposite the connector 424, may use three fasteners 460, as illustrated by the three apertures 464 in the end-clamp 452B. Two fasteners used in each of the end-clamps 454, and three fasteners used in each of the end clamps 452 are merely illustrative, and one or more fasteners may be equivalently used.

Figure 12:
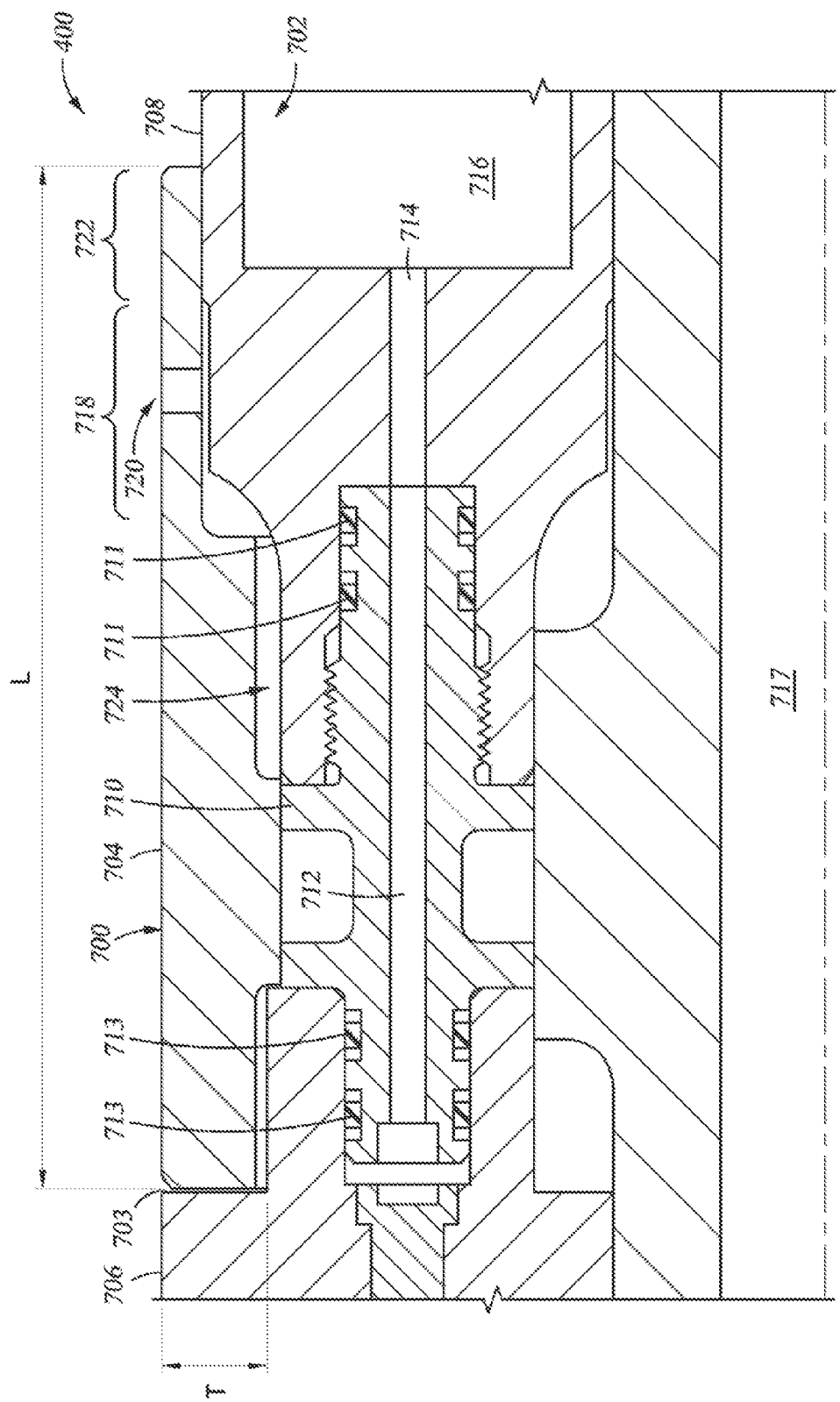
FIG. 12 shows a cross-sectional view of a sample bottle collar section proximate to a end-clamp in accordance with at least some embodiments.

FIG. 12 shows a cross-sectional view of the sample bottle drill collar 400 taken along the long axis of the drill collar, and proximate to an end-clamp on a connector 424 end of the sample bottle, in accordance with at least some embodiments. It is noted that the view of FIG. 12 is with the connector 424 protruding to the viewer's left, whereas in FIG. 10 the connector 424 protrudes to the viewer's right. In particular, illustrative end-clamp 700 couples to the drill collar within a recess 703. In one embodiment, an outer surface 704 of the end-clamp 700 is substantially flush with an outer surface of 706 of the drill collar, but in other embodiments the outer surface 704 may be raised slightly, or recessed slightly. The amount the end-clamp 700 may be raised above the outer surface 706 is less than or equal to 0.25 inch in particular embodiments. Likewise, the amount the outer surface 704 may be recessed less than or equal to 0.25 inches in particular embodiments.

The sample bottle assembly 702 as illustrated comprises a bottle portion 708 which is coupled to a connector portion 710 (which corresponds to the connector 424 of FIG. 10). Connector portion 710 seals to the remaining portions of the bottle assembly 702 by way of O-rings 711, and likewise seals to the remaining portions of the sample bottle drill collar section by way of O-rings 713. Other systems to seal the connector assembly may be equivalently used. The connector portion 710 may be integral with bottle assembly 702 (i.e., may be removed and installed as an integrated component with the bottle assembly 702), or the connector portion 710 may be separately installed and removed with each installation and removal of the bottle assembly 702. Formation fluids pumped and/or drawn into the bottle assembly 702 flow within flow bore 712 of the connector portion 710, and then within flow bore 714 to reach the chamber 716 defined by the bottle portion 708. Likewise, drilling fluid pumped from the surface to the bottom hole assembly 6 may flow through the central bore 717 of the collar section.

Still referring to FIG. 12, in particular embodiments a valve assembly is disposed in portion 718 of the bottle assembly 702, but the valve assembly is not shown so as not to unduly complicate the figure. The valve assembly may be opened and closed by insertion of a tool through the aperture 720 through the end-clamp 700. For example, prior to removal of the bottle assembly 702 from the pocket of the drill collar, the valve assembly may be actuated to seal the contents in the bottle portion 708 such that as the end-clamp 700 is removed and the bottle assembly 702 withdrawn from the pocket, the formation fluids do not escape from the chamber 716

The end-clamp 700 at least partially retains the bottle assembly in the pocket. In the particular embodiment, a portion of the end-clamp 700 abuts or overlaps the bottle assembly 702, as shown at portion 722. Although FIG. 12 shows the end-clamp 700 abutting only the largest diameter portion of the bottle assembly, in other embodiments the end-clamp 700 may be configured to contact or abut other portions of the bottle assembly, such a the neck portion 724, in addition to or in place of abutting the largest diameter portion. Further still, while FIG. 12 shows the end-clamp 700 directly abutting the bottle assembly 702 at portion 722, in other embodiments an elastomeric compound may reside between the overlapping portion 722 and the bottle assembly 702 to reduce the chances of damage to the exterior surface of the bottle assembly 702 during installation of the bottle assembly 702 in the pocket, during drilling, and/or during removal of the bottle assembly from the pocket.

In some embodiments, the axial length of the bottle assembly is approximately four feet in length, and the end-clamp 700 abuts a small portion of the overall axial length of the bottle assembly 702. In one embodiment, the end-clamp 700 abuts the bottle assembly 702 for four inches or less, but other lengths of the abutting portions may be equivalently used. With respect to the axial length of the end-clamp 700 (the length shown as "L" in FIG. 12), in some embodiments the end-clamp has an axial length that is less than one-quarter the length of the bottle assembly 702 (the entire length of the bottle assembly not shown). In particular embodiments, the axial length of the end-clamp 700 may be between and including six inches and twelve inches. Likewise, the illustrative end-clamp 700 has a thickness (the thickness shown as "T" in FIG. 12). In some embodiments the thickness of the end-clamp 700 is between and including 0.5 inch and 1.0 inch, but other thicknesses may be equivalently used. Moreover, and as illustrated in FIG. 12, the thickness may taper over the axial length. It is noted that the apertures 462 (FIG. 10) for the fasteners 460 (also FIG. 10) are not visible in FIG. 12. In some embodiments, the end-clamp 700 is constructed of metallic material (e.g., stainless steel), but other construction materials (e.g., non-stainless steel, steel coated with an elastomeric material, high density plastics) may be equivalently used.

FIG. 13 shows a cross-sectional view of the sample bottle drill collar section 400 taken along the central axis of the drill collar, and proximate to an end-clamp on an end opposite a connector 424 end of the sample bottle, in accordance with at least some embodiments. It is noted that the view of FIG. 13 would be the end opposite of the sample bottle assembly 702 in the view of FIG. 12. In particular, illustrative end-clamp 800 couples to the drill collar 404 within a recess 802. In one embodiment, an outer surface 804 of the end-clamp 800 is substantially flush with an outer surface of 806 of the drill collar (as shown in FIG. 12), but in other embodiments the outer surface 804 may be raised slightly, or recessed slightly. The amount the end-clamp 800 may be raised above the outer surface 806 is less than or equal to 0.25 inch in particular embodiments. Likewise, the amount the outer surface 804 is recessed less than or equal to 0.25 inches in particular embodiments.

The sample bottle assembly 702 on the end opposite the connector 424 (not shown in FIG. 13) comprises bottle portion 708 which is coupled to an end portion 810. End portion 810 seals the internal volume 716. Although FIG. 13 shows the end portion 810 integral with the bottle portion 708, in particular embodiments the end portion 810 is a separate component coupled to the bottle portion 708, such as by welding. In other embodiments, a valve assembly is disposed in end portion 810 of the bottle assembly 702, but the valve assembly is not shown so as not to unduly complicate the figure. The valve assembly, when present, may be opened and closed by insertion of a tool through the aperture 820 through the end-clamp 800. The valve assembly may be used in situations where the bottle assembly comprises an internal piston. As fluids are pumped into the bottle assembly, the piston moves thus expanding the volume on one side, and contracting the volume on the other side. The valve assembly is opened as when the bottle assembly is installed, and the fluids displaced as the piston moves escape through the valve assembly into the annulus.

The end-clamp 800 at least partially retains the bottle assembly in the pocket. In the particular embodiment, a portion of the end-clamp 800 abuts or overlaps the bottle assembly 702, as shown at portion 822. Although FIG. 13 shows the end-clamp 800 abutting only the largest diameter portion of the bottle assembly, in other embodiments the end-clamp 800 may be configured to contact or abut other portions of the bottle assembly, such a the reduced diameter portion 824, in addition to or in place of abutting the largest diameter portion. Further still, while FIG. 13 shows the end-clamp 800 directly abutting the bottle assembly 702 at portion 822, in other embodiments an elastomeric compound or material may reside between the overlapping portion 822 and the bottle assembly 702 to reduce the chances of damages to the exterior surface of the bottle assembly 702 during installation of the bottle assembly 702 in the pocket, during drilling, and/or during removal of the bottle assembly from the pocket.

Still referring to FIG. 13, in the particular cross-section shown, the end-clamp 800 comprises a fastener aperture 830 within which a fastener 832 is inserted. The fastener 832, such as a threaded hex-head bolt, abuts a shoulder 834 within the aperture 830, and likewise couples by way of mating threads (the threads not specifically shown) to the drill collar 404. In some embodiments, an O-ring 836 forms a seal between the fastener 832 and the drill collar 404 to reduce invasion of drilling fluids into region between the threads of the fastener 832 and the mating threads in the drill collar 404. Also with regard to sealing, in particular embodiments, and as shown in FIG. 13, the end portion 810 of the bottle assembly 702 has an O-ring 840 that seals to the end-clamp 800 to reduce the invasion of drilling fluids into the region 842 between the bottle assembly 702 and end-clamp 800.

In some embodiments, the axial length of the bottle assembly is approximately four feet in length, and the end-clamp 800 abuts a small portion of the overall axial length of the bottle assembly 702. In one embodiment, the end-clamp 800 abuts the bottle assembly 702 for four inches or less, but other lengths of the abutting portions may be equivalently used. With respect to the axial length of the end-clamp 700 (the length shown as "L" in FIG. 13), in some embodiments the end-clamp has an axial length that is less than one-quarter the length of the bottle assembly 702. In particular embodiments, the axial length of the end-clamp 800 may be between and including six inches and twelve inches. Likewise, the illustrative end-clamp 800 has a first thickness (the thickness shown as "T1" in FIG. 13). In some embodiments the thickness T1 of the end-clamp 800 is between and including 1.0 inch and 2.0 inches, but other thicknesses may be equivalently used. Moreover, and as illustrated in FIG. 13, the thickness may taper over the axial length, such that the thickness T2 at the distal end of the end-clamp is less than the thickness T1. In some embodiments, the thickness T2 of the end-clamp 800 is between and including 0.5 inch to 1.0 inch.

Given that the axial lengths of the end-clamps of the various embodiments are less than an axial length of the bottle assembly, in some embodiments the bottle assembly 702 is visible through the aperture. Referring again briefly to FIG. 10, as illustrated the end-clamps 452 and 454 abut only a portion of the bottle assemblies 410, and thus the bottle assembles 410, in these embodiments, are exposed through their respective apertures 402. In some cases it is advantageous to have the bottle assemblies exposed. For example, each bottle assembly 410 may carry a unique identification mechanism (e.g., serial number, bar code, radio frequency identification tag), and having the bottle assemblies exposed through the apertures 418 makes observing and/or reading the identification mechanisms possible and/or easier.

However, in spite of the advantages to having the bottle assemblies exposed, the exposure of the bottle assemblies 410 in the nature of FIG. 10 may lead to other concerns. For example, the somewhat long spans of the bottle assemblies 410 between the end-clamps 452 and 454 may lead to various vibration modes of the bottle assemblies in some drilling instances. Moreover, the drilling fluid, along with drill cuttings in some instances, tends to seep behind the bottle assemblies 410, particularly if the bottle assemblies are oscillating in one or more vibration modes. The vibration modes may also result in unwanted agitation or mixing of the sampled fluids. Moreover, the piston internal to the sample bottle assembly, when exposed to vibration, is more likely to leak across its seals, or more likely to develop leaking seals, The specification now turns to various methods and related systems to reduce the vibration of bottle assemblies and related shortcomings.

FIG. 14 shows a perspective view of a sample bottle drill collar section 800 in accordance with at least some embodiments. In particular, the sample bottle drill collar section 800 comprises a drill collar 801 that defines an outer surface 802. The drill collar 801 further defines a plurality of pockets accessible through apertures in the drill collar 801, and the view of FIG. 14 shows pockets 804 (in particular 804A and 804B) accessible through respective apertures 806 (in particular 806A and 806B). While in the view of FIG. 14 only two pockets are visible, additional pockets accessible through additional apertures may reside on the back side of the drill collar 801. Within each pocket 804 resides a sample bottle assembly 808 (in particular 808A and 808B), which bottle assemblies may be the same as bottle assemblies 410 of FIG. 10 and/or bottle assemblies 702 of FIGS. 12 and 13. Each bottle assembly is at least partially held in place by end-clamps 810 and 812. End-clamp 812A is shown in exploded view to illustrate a recess 814 within which the end-clamp 812A resides. Other end-clamps likewise have their respective recesses.

In order to at least partially retain the bottle assemblies 808 within their respective pockets 804 and/or reduce vibration of the bottle assemblies 808, the embodiments illustrated by FIG. 14 further comprise intermediate clamps. In some situations, a single intermediate clamp 816 is used, but in embodiments where intermediate clamps are desired, one or more intermediate clamps are contemplated. FIG. 14 shows a configuration of the sample bottle drill collar section 800 that comprises two intermediate clamps; however, for purposes of the discussion the second intermediate clamp 818 is shown separated from the collar section 800. Intermediate clamp 816 couples to the outer surface 802 of the drill collar 801. The intermediate clamp 816 circumferentially spans at least one pocket 804, and as illustrated the intermediate clamp 816 circumferentially spans each pocket 804 defined by the drill collar 801. In accordance with at least some embodiments, each intermediate clamp couples to the outer surface 802 by way of a channel or reduced diameter portion, as illustrated by reduced diameter portion 820 for clamp 818. In some embodiments the reduced diameter portion for each clamp circumscribes the drill collar 801. In some cases the exterior surface defined by an intermediate clamp (e.g., exterior surface 822 of intermediate clamp 816) coincides with the largest outside diameter portion of the outer surface 802. In other cases, however, the exterior surface 822 may define an outside diameter greater than the outer surface 802, or the exterior surface 822 may define an outside diameter smaller than the outer surface 802.

Still referring to FIG. 14, the axial length of each intermediate clamp is less than axial length of each sample bottle assembly 808. For example, the axial length, shown as "L" in the figure, of intermediate clamp 816 is less that an axial length of the bottle assembly 808A within the pocket 804A (the bottle assembly axial length not specifically shown). In some cases, the axial lengths of each intermediate clamp 816, 818 are about four inches, but longer and shorter axial lengths may be equivalently used. Moreover, each intermediate clamp has a thickness, such as thickness T shown with respect to intermediate clamp 818. In some embodiments, the thickness T is one-quarter of inch, but thicker and thinner thicknesses of the intermediate clamps may be equivalently used. Moreover, as discussed more below, each intermediate clamp may have conformal surfaces that conform to underlying structures, such as the bottle assembly, and thus need not have a uniform thickness. The reduced diameter portion within which each intermediate clamp resides has a depth that corresponds to the thickness of the intermediate clamp that couples within the reduced diameter portion.

The illustrative intermediate clamps of FIG. 14 are shown with constant axial length around their entire circumference. However, having constant axial length is not required. FIG. 15 shows alternative embodiments where the axial length of the intermediate clamps varies. In particular, illustrative intermediate clamp 840 has extensions or tabs 842 that define increased axial length portions of the clamp. Each tab is configured to extend over, abut and at least partially retain an underlying bottle assembly within its respective slot. The tab-embodiments of intermediate clamp 840 may be used, for example, in situations where a single intermediate clamp is used, or perhaps in situations where the underlying sample bottle assembly is particularly susceptible to vibration. In some cases the intermediate clamp 840 is configured to have a set of tabs for each sample bottle assembly to be retained. Conversely, FIG. 15 also shows alternative embodiments where the axial length of the intermediate clamp shortens or narrows. In particular, illustrative intermediate clamp 844 defines slots 846. Each slot further exposes the underlying sample bottle assembly. The slot-embodiments of intermediate clamp 844 may be used, for example, in situation where less bottle vibration is expected, or where other mechanism (such as the spacer embodiments discussed below) may be additionally used to retain the sample bottle assembly in the respective pockets.

Figure 16:
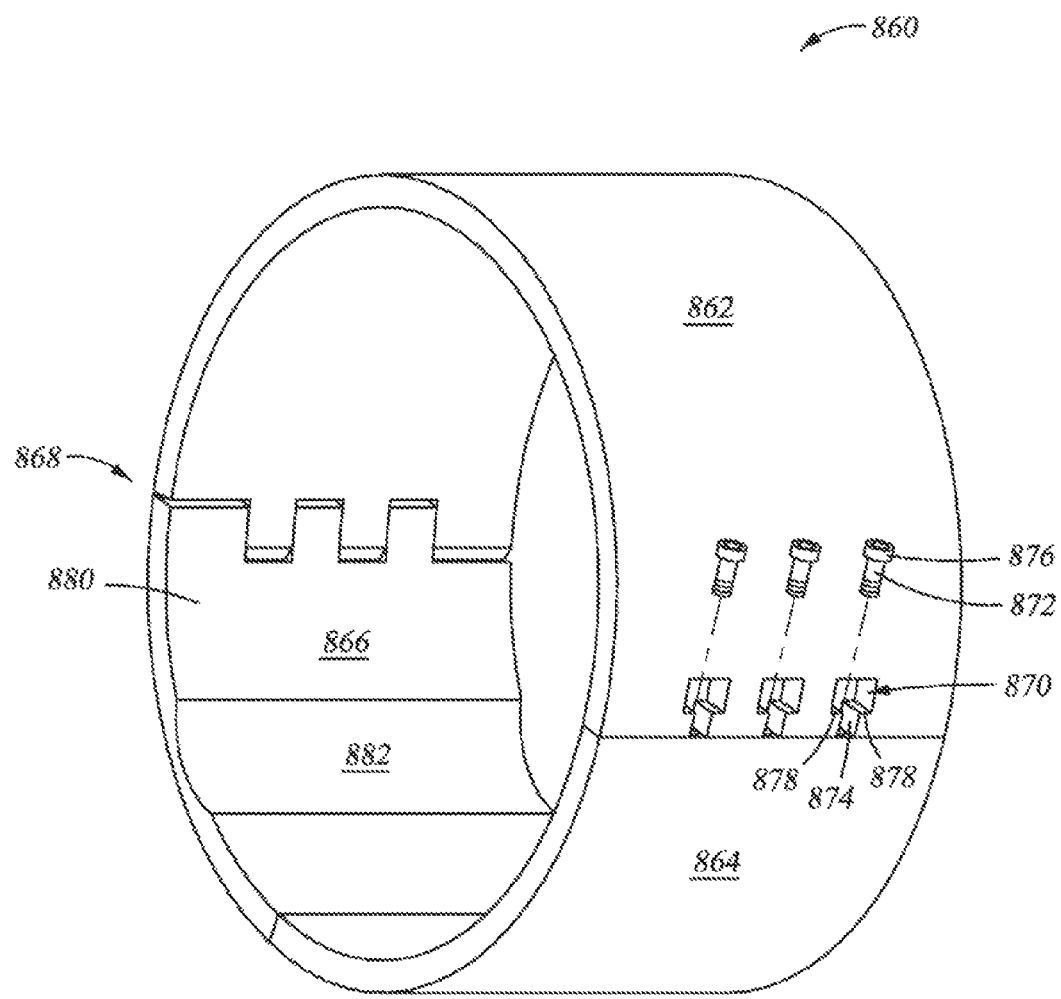
FIG. 16 shows a perspective view of an intermediate clamp in accordance with at least some embodiments.

The mechanical relationship of the various components of the intermediate clamps, such that the clamps can be selectively installed and removed from the sample bottle collar section, may take any suitable form. In the particular embodiments illustrated, each intermediate clamp has three semicircular portions coupled to create the entire circumferential clamp. FIG. 16 shows, in greater detail, an intermediate clamp in accordance with at least some embodiments to further describe one illustrative arrangement. In particular, the illustrative intermediate clamp 860 comprises three semicircular components 862, 864 and 866. In the embodiments illustrated semicircular component 862 is hinged to semicircular component 866 by way of hinge portion 868. Further in the illustrative embodiment, semicircular portion 826 couples to the semicircular portion 864 by way of a plurality of fasteners. In particular, portion 862 has a plurality of T-slots, such as T-slot 870. A fastener 872 threadingly couples to the semi-circular portion 864 by extending through the narrow portion 874 of the T-slot 870. The head 876 of the fastener 872 abuts the shoulder portions 878 of the T-slot 870, and thus as the fastener 827 is tightened, the fastener biases the semi-circular portion 862 against the semi-circular portion 864. The remaining T-slots work similarly.

It is noted that the specific arrangement of the T-slots may be reversed (i.e., the T-slots on the semicircular portion 864 and the fasteners threadingly coupled to the semicircular portion 862). The coupling between semicircular portion 866 and semicircular portion 864 may be either a hinged connection or a connection by way of fasteners. Moreover, three semicircular portions are merely illustrative, as two more semicircular portions may be equivalently used to construct a clamp that circumscribes the underlying drill collar. In yet still other cases, the semicircular portions couple to the underlying drill collar, such as by fasteners. That is, rather than the fasteners biasing the semicircular portions toward each other, the fasteners threadingly couple to the drill collar, and hold the semicircular portion (or portions) against the outer surface of the drill collar. Further still, the material from which the intermediate clamps are constructed may vary. While in many embodiments the clamps are metallic (e.g., stainless), other materials (e.g., high density plastics, fiberglass composite materials), may be equivalently used.

FIG. 16 further illustrates that the internal diameter of an intermediate clamp may be configured to abut underlying portions in a conformal manner. In particular, the internal diameter 880 of the illustrative clamp 860 comprises a conformal section 882. In the particular example of FIG. 16, the conformal section 882 is semicircular and designed and constructed to conformally abut an underlying sample bottle assembly that, in this example, has a circular cross-section. A sample bottle assembly may take any cross-sectional shape, and thus the conformal section 882 may likewise be modified to conformally abut any cross-sectional shape. It is noted, before proceeding, that the end-clamps and intermediate clamps (if present) also provide suitable locations for applying straps and/or chains in the transport of the sample bottle drill collar sections to and from drilling locations.

In spite of the end-clamps and any intermediate clamps used to retain a sample bottle assembly in a pocket, drilling fluid may still tend to seep or invade the area behind the sample bottle assembly within a pocket. Likewise, in some operational situations end-clamps, and one or more intermediate clamps if used, may be deemed insufficient to retain with a desired rigidity a sample bottle assembly in the pocket. Thus, in accordance with at least some embodiments one or more spacers are used in conjunction with the one or more clamps to at least partially retain a sample bottle assembly in a pocket, to reduce the invasion of drilling fluid behind the sample bottle assemblies, and/or to reduce vibration.

Figure 17:
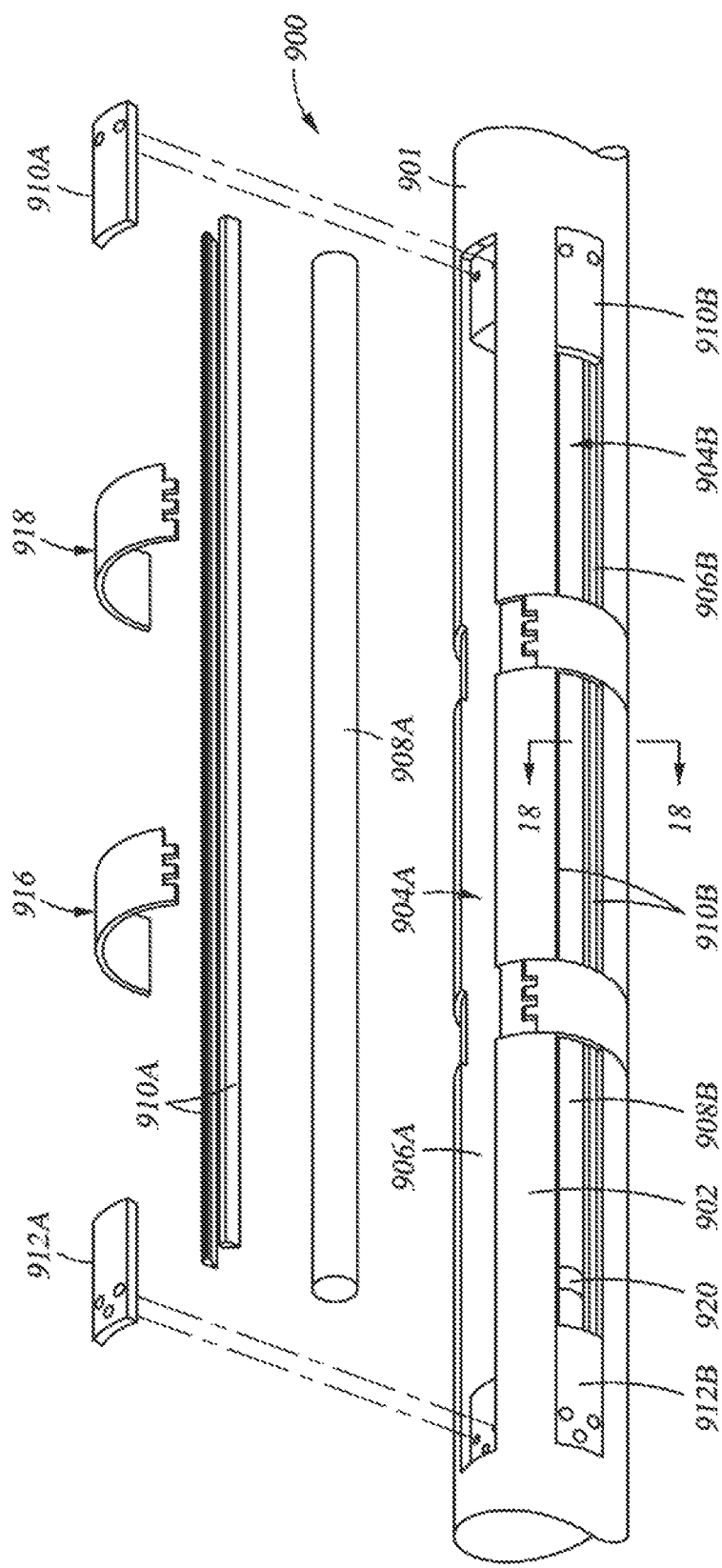
FIG. 17 shows a perspective, partially exploded, view of a sample bottle collar section in accordance with at least some embodiments.

FIG. 17 shows a perspective, partial exploded view, of a sample bottle drill collar section 900 in accordance with at least some embodiments. In particular, the sample bottle drill collar section 900 comprises drill collar 901 that defines an outer surface 902. The drill collar 901 defines a plurality of pockets accessible through apertures in the drill collar 901, and the particular view of FIG. 17 shows pockets 904 (in particular 904A and 904B) accessible through respective apertures 906 (in particular 906A and 906B). While in the view of FIG. 17 only two pockets are visible, additional pockets accessible through additional apertures may reside on the back side of the drill collar 901. Within each pocket 904 resides a sample bottle assembly 908 (in particular 908A and 908B), which bottle assemblies may be the same as bottle assemblies 410 of FIG. 10, sample bottle assemblies 808 of FIG. 14, and/or sample bottle assemblies 702 of FIGS. 12 and 13. Each sample bottle assembly is at least partially held in place by end-clamps 910 and 912. Components associated with pocket 904A are shown in exploded view so as to further describe the inter-relationship.

In order to at least partially retain the bottle assemblies 908 within their respective pockets 904, the embodiments illustrated by FIG. 17 further comprise a set of spacers 910 (in particular 910A and 910B). As illustrated, the spacers 910 are disposed within their respective pockets 904. As implied by the exploded view portion of FIG. 17, the spacers abut the bottle assembly 908, and also abut side walls of the pocket 904. The spacers have an axial length greater than half an axial length of the sample bottle assembly 908, and as illustrated have axial length substantially the same as the sample bottle assembly 908. Having "substantially" the same length as the sample bottle assembly in the context of the spacers shall mean that the spacers are long enough to extend under the end-clamps, and in most cases have an axial length within ten percent (10%) of the length of the sample bottle assembly excluding connectors and/or valve portions.

In accordance with the illustrated embodiments, the spacers 910 are composed of two individual components disposed on each side of the sample bottle assembly 908. In this way, and as particularly shown with respect to sample bottle assembly 908B, the sample bottle assembly 908B is visible in the area between the spacers 910. In other embodiments, the spacers 910 may be coupled by one or more cross-members, such as cross-member 920 associated with spacers 910B. The physical materials from which the spacers 910 are made varies. In some cases, the spacers 910 are metallic (e.g., stainless steel). In other embodiments, the spacers are made from a high density plastic, such as in an extrusion process or by way of injection molding. In still other embodiments, the spacers 910 are made of materials such as fiberglass and/or carbon fiber reinforced epoxy.

Still referring to FIG. 17, the illustrative embodiments further comprises intermediate clamps 916 and 918, with a portion of the intermediate clamps shown in exploded form. Thus, the spacers 910 reside under the intermediate clamps 916 and 918, and in some cases an internal diameter of each intermediate clamp has a conformal section to abut an outer surface of the spacers. In some embodiments, the intermediate clamps may be omitted, particularly where the axial length of the sample bottle assemblies 910 are relatively short (e.g., two feet or less), or where the spacers have high rigidity (e.g., the spacers are metallic). In other embodiments, the spacers may be present, but the spacers may not have sufficient axial length to reside under, and thus be retained by, the end-clamps 910, 912. In embodiments where the spacers 910 do not extend under the end-clamps 910, 912, the spacers may be retained in the pocket exclusively by one or more intermediate clamps 916, 918.

Figure 18:
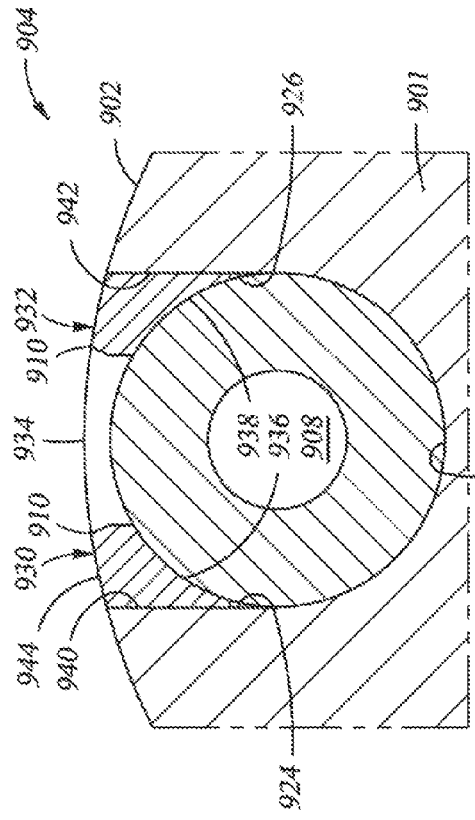
FIG. 18 shows a cross-sectional view, taken substantially along lines 18-18 of FIG. 17, in accordance with at leas some embodiments.

FIG. 18 shows a cross-sectional view of the spacer embodiments taken substantially along line 18-18 of FIG. 17. In particular, FIG. 18 shows a portion of the drill collar 901 comprising pocket 904 that defines a first side wall 924 and a second side wall 926. In the particular example of FIG. 18, the sidewalls 924 and 926 of the pocket 904 are parallel, and are connected by way of a semicircular bottom wall 928. However, having a semicircular bottom wall 928 is merely illustrative, and other cross-sectional shapes for the bottom wall (e.g., a bottom wall that defines a plane that is normal at least one sidewall), may be equivalently used. FIG. 18 further shows spacers 910, and in the view of FIG. 18 spacers 910 comprise left spacer 930 and right spacer 932. Further still, FIG. 18 shows bottle assembly 908 residing within the pocket 904 under the spacers 910 and clamp portion 934. In the particular view of FIG. 18, clamp portion 934 is a portion of intermediate clamp 916.

Left spacer 930 defines a conformal surface 936 that abuts and conforms to the cross-sectional shape of the sample bottle assembly 908, which in the illustrative embodiments is circular. Likewise, right spacer 932 defines a conformal surface 938 that abuts and conforms to the cross-sectional shape of the sample bottle assembly 908. Left spacer 930 further comprises wall surface 940 that abuts sidewall 924, and right spacer 932 further comprises a wall surface 942 that abuts sidewall 926. Further still, the left spacer 930 defines an outer surface 944, and right spacer 932 defines an outer surface 946. As illustrated, the outer surfaces 944, 946 coincide with the outer surface 902 of the drill collar 901. However, in other embodiments, the outer surfaces of the 930 and 932 may extend beyond the outer surface 902 of the drill collar 901, or may reside below the outer surface 902 of the drill collar 901.

The various embodiments discussed above with respect to spacers, again, help retain the sample bottle assembly in the pocket, reduce invasion of drilling fluid behind the sample bottle assembly, and/or reduce vibration and the adverse effects associated therewith (e.g., mixing of fluid samples, leaking of piston with the sample bottle assembly). However, in accordance with yet still further embodiments, adhesives are used in conjunction with the one or more clamps to at least partially retain a sample bottle assembly in a pocket, to reduce the invasion of drilling fluid behind the sample bottle assemblies, and/or to reduce vibration.

Figure 19:
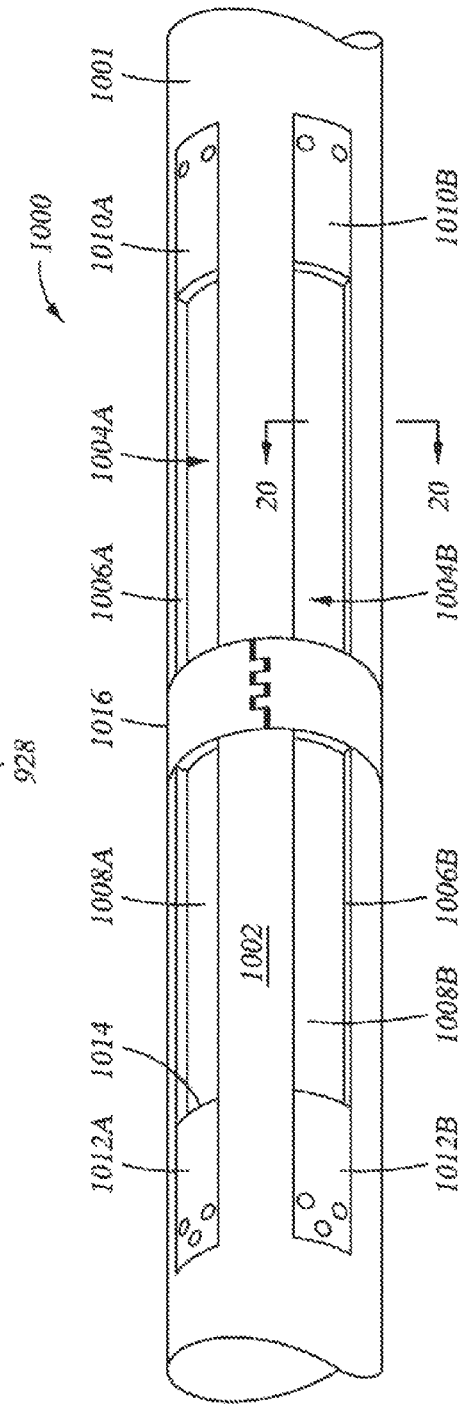
FIG. 19 shows a perspective view of a sample bottle collar section in accordance with at least some embodiments.

FIG. 19 shows a perspective view of a sample bottle drill collar section 1000 in accordance with at least some embodiments. In particular, the sample bottle drill collar section 1000 comprises drill collar 1001 that defines an outer surface 1002. The drill collar 1001 defines a plurality of pockets accessible through apertures in the drill collar 1001, and the particular view of FIG. 19 shows pockets 1004 (in particular 1004A and 1004B) accessible through respective apertures 1006 (in particular 1006A and 1006B). While in the view of FIG. 19 only two pockets are visible, additional pockets accessible through additional apertures may reside on the back side of the drill collar 1001. Within each pocket 1004 resides a sample bottle assembly, but in the embodiments of FIG. 19 the sample bottle assemblies are not visible because the sample bottle assemblies are covered and/or submerged in an adhesive 1008 (in particular 1008A and 1008B). Each sample bottle assembly is at least partially held in place by end-clamps 1010 and 1012. Moreover, the sample bottles assemblies are also at least partially held in place by coupling to the adhesive 1008. As illustrated in FIG. 19, the adhesive extends from the end-clamp 1010 to end-clamp 1012, and in some embodiments extends under the end-clamps. In some situations, the adhesive also reduces vibration, and provide an insulating quality to reduce the temperature extremes experienced by the sample bottle assembly.

In accordance with at least some embodiments, the adhesive is applied to the pocket 1004 after a sample bottle assembly has been inserted in the pocket 1004. Thereafter, the adhesive is allowed to cure (i.e., harden). If the adhesive extends under the end-clamps, the end-clamps are installed after application of the adhesive. In some cases, the end-clamps may be installed after application of the adhesive, but before the adhesive hardens, such that the adhesive may additionally adhere to the end-clamps. In embodiments where the adhesive merely abuts the end-clamps on their distal ends (e.g., distal end 1014 of end-clamp 1012A), the end-clamps are installed before the adhesive is applied. While FIG. 19 also shows an intermediate clamp 1016, in other embodiments the intermediate clamp 1016 may be omitted, or a plurality of intermediate clamps may be used. When present, the intermediate clamp 1016 may be installed after application of the adhesive. In other cases, the intermediate clamp 1016 may be installed after application of the adhesive, but before the adhesive hardens, such that the adhesive may additionally adhere to the intermediate clamp 1016.

In accordance with at least some embodiments, the adhesive is an epoxy, such as a two part epoxy that hardens a certain amount of time after the components are mixed. In further embodiments, the epoxy may be reinforced, such as with sand, fiberglass or carbon-fiber reinforcement. In some circumstances, the epoxy may experience damage during use. Less damage is expected in wireline logging uses, and more damage is expected in MWD/LWD operations. In most cases, the adhesive will be sufficiently resilient to protect the underlying sample bottle assembly in spite of the damage. However, in cases where damage is excessive (e.g., deviated drilling where the collar sections are expected to regularly contact the borehole wall), the adhesive may be reapplied in the field. Reapplication may be merely reapplication over the damaged adhesive, of the damaged adhesive removed and a full new set of adhesive applied. In other cases, the adhesive 1008 is putty that hardens on contact with air, such as clay-based putty. In other case, the adhesive 1008 is an elastomeric compound the cures to a deformable but resilient character, like rubber.

FIG. 20 shows a cross-sectional view of the adhesive embodiments taken substantially along line 20-20 of FIG. 19. In particular, FIG. 20 shows a portion of the drill collar 1001 comprising pocket 1004 that defines a first side wall 1024 and a second side wall 1026. In the particular example of FIG. 20, the sidewalls 1024 and 1026 of the pocket 1004 are parallel, and are connected by way of a semicircular bottom wall 1028. However, having a semicircular bottom wall 1028 is merely illustrative, and other cross-sectional shapes for the bottom wall (e.g., a bottom wall that defines a plane that is normal at least one sidewall), may be equivalently used. FIG. 20 further shows adhesive 1008. Further still, FIG. 18 shows bottle assembly 1028 residing within the pocket 1004 under the adhesive 1008. In the particular view of FIG. 20, clamp portion 1030 could be a portion of an intermediate clamp 1016 if present, or end-clamp 1012B if the intermediate clamp is not present.

The adhesive 1008 abuts the first sidewall 1024, the second sidewall 1026 and the sample bottle assembly 1028. As illustrated, the sample bottle assembly 1028 is covered and/or submerged within the adhesive. However, in other embodiments portions of the sample bottle assembly 1028 may be left uncovered by the adhesive. Further, the adhesive defines an outer surface 1032 which, as illustrated, resides below the outer surface 1002 of the drill collar 1001. However, in other embodiments, during application of the adhesive forms may be used to extend the outer surface 1032 of the adhesive above the outer surface 1002 of the drill collar 1001, and in yet still other embodiments forms may be used during application such that the outer surface 1032 of the adhesive 1008 coincides with the outer surface 1002 of the drill collar 1001.

The various embodiments discussed to this point have been in relation to mechanisms to retain a sample bottle assembly in a pocket. However, the sample bottle assembly itself may take many forms, and each is operational with the each of the embodiments discussed above.

FIG. 21 shows both a perspective view, and an exploded perspective view, of a sample bottle assembly in accordance with at least some embodiments. In particular, FIG. 21 shows two versions of sample bottle assembly 1100. With respect to the exploded view, the sample bottle assembly 1100 comprises a sample bottle 1102. The sample bottle 1102 has side walls that define an interior volume, and it is within the interior volume that fluid samples drawn from the formation are stored. Coupled to the sample bottle 1102 is a neck portion 1104, which corresponds in some case to the neck portion 724 (FIG. 13). The sample bottle 1102 defines an axial length indicated as L1 in FIG. 21. In some cases, the axial length L1 is four feet, but shorter axial lengths (e.g., two feet) and longer axial lengths may be equivalently used.

In accordance with at least some embodiments, the sample bottle assembly 1100 further comprises a sleeve 1106. The sleeve 1106 comprises a bore 1108. In the illustrative embodiments of FIG. 21, the bore 1008 is a central bore along the central axis of the 1110 of the sleeve, but bores along other than the central axis may be equivalently used. The sleeve 1106 also defines an axial length, indicated as L2 in FIG. 21. In some cases, the axial length L2 is substantially the same as the axial length L1 of the sample bottle. The sleeve 1106 having "substantially" the same axial length as the sample bottle 1102 in the context of the sample bottle assembly shall mean that the sleeve is long enough to extend under the end-clamps, and in most cases have an axial length within ten percent (10%) of the length of the sample bottle 1102. In some cases the axial length of the sleeve 1106 is four feet, but shorter axial lengths (e.g., two feet) and longer axial lengths may be equivalently used.

In accordance with the illustrated embodiments, the sample bottle 1102 is telescoped within the sleeve 1106, as shown by the lower perspective view of FIG. 21. The sleeve serves to protect the sample bottle 1102, which is a pressure vessel, from damage such as nicks and cuts which degrade the structural integrity of the sample bottle 1102. In some cases the internal diameter of the sleeve 1106 is sufficiently large to enable the sample bottle to be easily telescoped into and out of the sleeve, such as by hand. In yet still other cases, the inside diameter 1108 of the sleeve 1106 is such that the sample bottle 1102 is friction fit within the sleeve (e.g., such as by hydraulic press, thermally expanding the sleeve 1106, and/or thermally shrinking the sample bottle 1102). In some embodiments, the outside diameter of the sample bottle 1102 is two inches, but larger diameter sample bottles, and smaller diameter sample bottles (e.g., one inch, 0.5 inch) may be equivalently used. The sleeve not only protects the sample bottle from damage, but also makes the overall assembly more rigid, thus reducing vibration. Moreover, the sleeve has an insulating effect, which reduces the temperature extremes to which the bottle assembly is exposed.

The materials which make up the sleeve 1106 are many. In some embodiments, the sleeve 1106 is metallic (e.g., stainless steel). In other embodiments, the sleeve may be a high density plastic material. In yet still other embodiments, the sleeve 1106 may be a fiberglass reinforced or carbon fiber reinforced epoxy material. In yet still other embodiments, the sleeve may have a core of a first material (e.g., steel), and be coated by second material (e.g., an elastomeric material).

The sleeve embodiments are particularly useful in combination with the adhesive embodiments. In particular, in situations where the adhesive is applied to a sample bottle assembly without a sleeve, the adhesive adheres directly to the bottle assembly. It may be difficult, in some circumstances, to remove sample bottle assembly because of the adhesive; however, in embodiments where the sample bottle assembly comprises a sleeve, the sleeve may comprise one or more features to assist in removing the sample bottle assembly from the pocket. Returning briefly to FIG. 21, FIG. 21 shows features 1140 coupled to the sleeve 1106, the features 1140 couple, for example by welding. Welding or otherwise attaching features 1140 to the bottle 1102 may not be possible, given that the bottle 1102 is a pressure vessel. The features 1140 are shown as extensions that, in some embodiments, extend above an upper surface of the adhesive. For purposes of this disclosure and the claims, having features 1140 coupled to the sleeve 1106, where the features extend above the upper surface of the adhesive and are designed and constructed to assist removing the sample bottle assembly used with the adhesive embodiments, shall not obviate the status of a sample bottle assembly as being covered and/or submerged by the adhesive. In some cases the features have internal threads to which additional handles or pulling mechanisms may be attached. The internal threads may be protected during drilling operations by a cap or screw.

FIG. 22 shows a cross-sectional view of the sample bottle assembly taken substantially along line 22-22 of FIG. 21. In particular, FIG. 22 shows the sample bottle 1102 defining an interior volume 1112, and also the sleeve 1106. As illustrated in FIG. 22, in some cases both the sample bottle 1102 and the sleeve 1106 define a circular cross-section, but other cross-sectional shapes may be equivalently used. For example, FIG. 23 shows a cross-sectional view of a sample bottle assembly where the sleeve 1106 has an outside surface that has a cross-section that defines a conformal surface to a pocket within which the sample bottle assembly may be placed, such as cross-sectional shape of pocket 904 of FIG. 18, and/or cross-sectional shape of pocket 1004 of FIG. 20.

Figure 24:
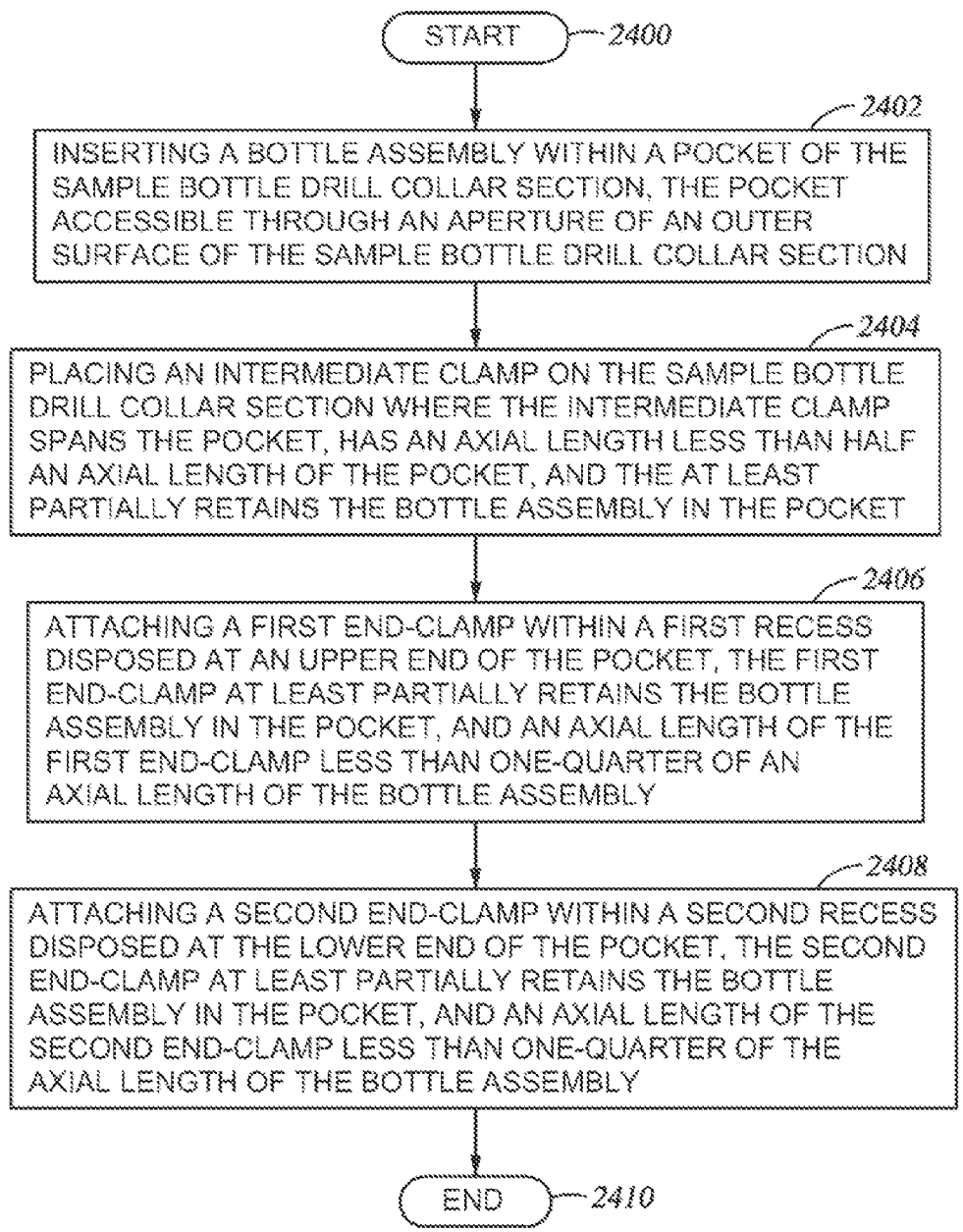
FIG. 24 shows a method in accordance with at least some embodiments.

FIG. 24 shows a method in accordance with at least some embodiments. In particular, the method starts (block 2400) and proceeds to inserting a bottle assembly within a pocket of the sample bottle drill collar section (the pocket accessible through an aperture of an outer surface of the sample bottle drill collar section) (block 2402). The illustrative method then proceeds to placing an intermediate clamp on the sample bottle drill collar section where the intermediate clamp spans the pocket, has an axial length less than half an axial length of the pocket, and the at least partially retains the bottle assembly in the pocket (block 2404). Further, the method comprises attaching a first end-clamp within a first recess disposed at an upper end of the pocket, the first end-clamp at least partially retains the bottle assembly in the pocket, and an axial length of the first end-clamp less than one-quarter of an axial length of the bottle assembly (block 2406). Finally, the illustrative method comprises attaching a second end-clamp within a second recess disposed at the lower end of the pocket, the second end-clamp at least partially retains the bottle assembly in the pocket, and an axial length of the second end-clamp less than one-quarter of the axial length of the bottle assembly (block 2408), and the method ends (block 2410).

Figure 25:
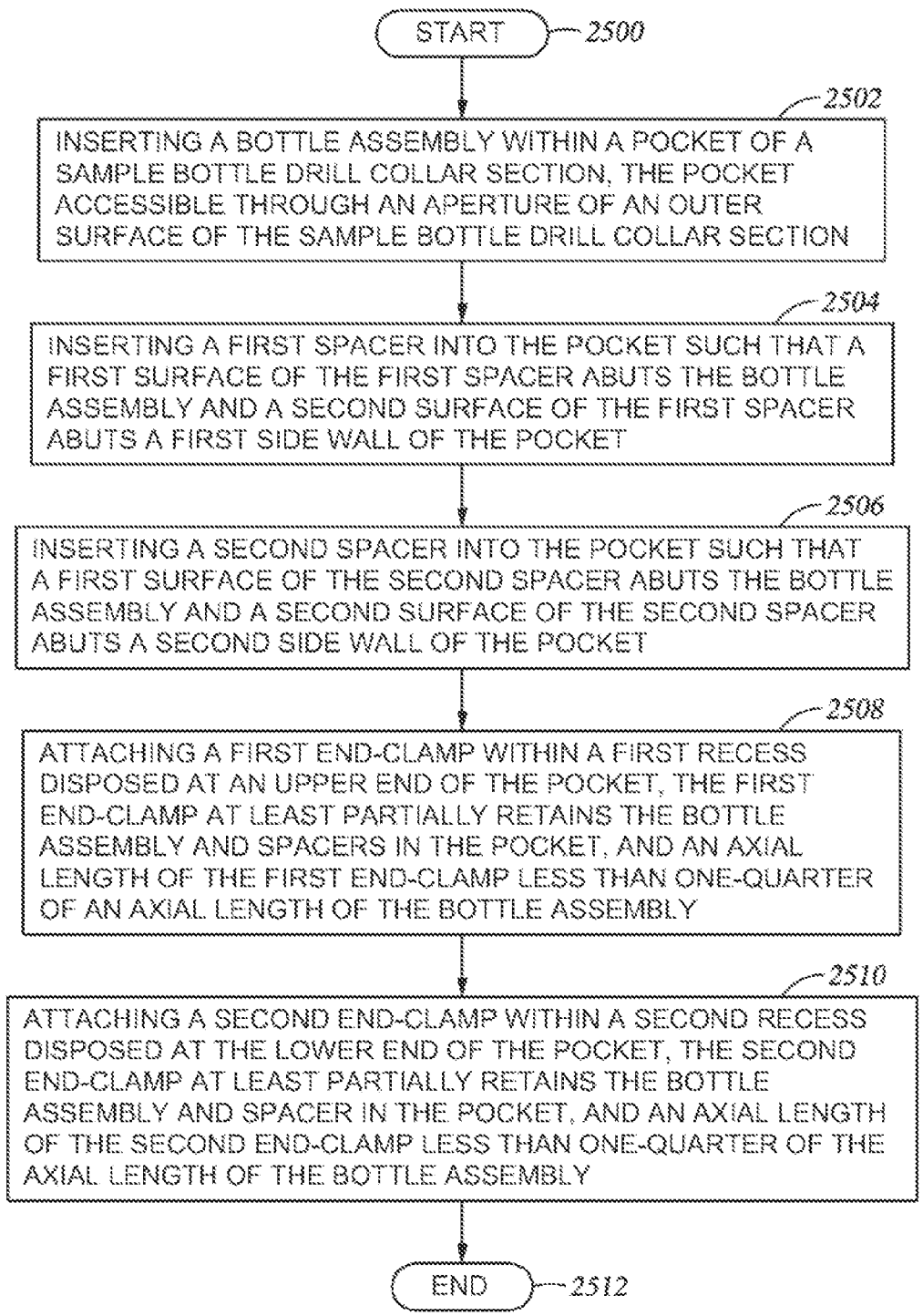
FIG. 25 shows a method in accordance with at least some embodiments.

FIG. 25 also shows a method in accordance with at least some embodiments. In particular, the method starts (block 2500), and proceeds to inserting a bottle assembly within a pocket of a sample bottle drill collar section (the pocket accessible through an aperture of an outer surface of the sample bottle drill collar section) (block 2502). And then the method comprises inserting a first spacer into the pocket such that a first surface of the first spacer abuts the bottle assembly and a second surface of the first spacer abuts a first side wall of the pocket (block 2504), and inserting a second spacer into the pocket such that a first surface of the second spacer abuts the bottle assembly and a second surface of the second spacer abuts a second side wall of the pocket (block 2506). The method further comprises attaching a first end-clamp within a first recess disposed at an upper end of the pocket, the first end-clamp at least partially retains the bottle assembly and spacers in the pocket, and an axial length of the first end-clamp less than one-quarter of an axial length of the bottle assembly (block 2508). Finally, the illustrative method comprises attaching a second end-clamp within a second recess disposed at the lower end of the pocket, the second end-clamp at least partially retains the bottle assembly and spacers in the pocket, and an axial length of the second end-clamp less than one-quarter of the axial length of the bottle assembly (block 2510), and the method ends (block 2512).

Figure 26:
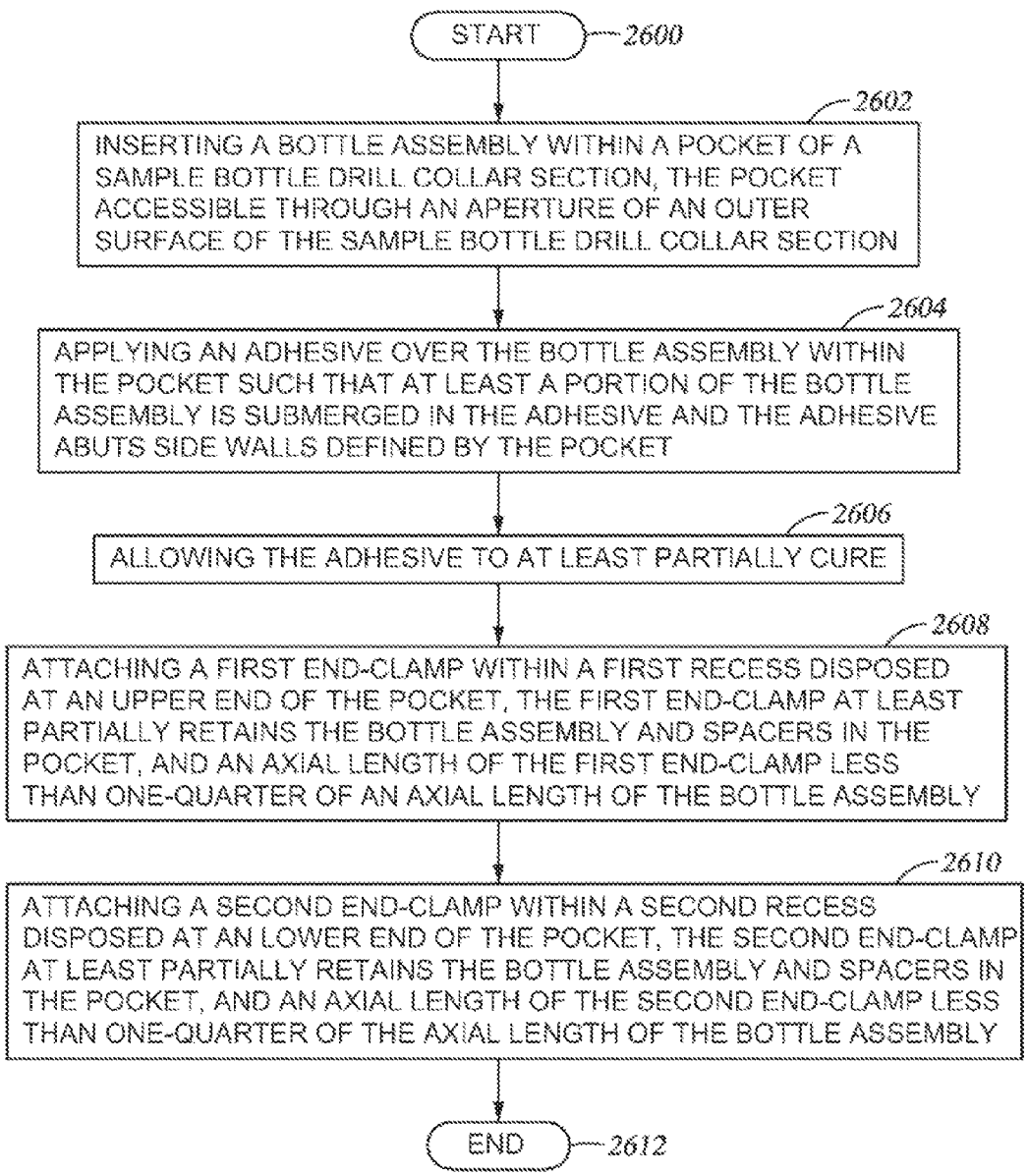
FIG. 26 shows a method in accordance with at least some embodiments.

FIG. 26 shows a method in accordance with at least some embodiments. In particular, the method starts (block 2600) and proceeds to inserting a bottle assembly within a pocket of a sample bottle drill collar section, the pocket accessible through an aperture of an outer surface of the sample bottle drill collar section (block 2602). Further the method comprises applying an adhesive over the bottle assembly within the pocket such that at least a portion of the bottle assembly is submerged in the adhesive and the adhesive abuts side walls defined by the pocket (block 2604), and then allowing the adhesive to at least partially cure (block 2606). The method further comprises attaching a first end-clamp within a first recess disposed at an upper end of the pocket, the first end-clamp at least partially retains the bottle assembly and spacers in the pocket, and an axial length of the first end-clamp less than one-quarter of an axial length of the bottle assembly (block 2608). Finally, the illustrative method comprises attaching a second end-clamp within a second recess disposed at the lower end of the pocket, the second end-clamp at least partially retains the bottle assembly and spacers in the pocket, and an axial length of the second end-clamp less than one-quarter of the axial length of the bottle assembly (block 2610), and the method ends (block 2612).

Figure 27:
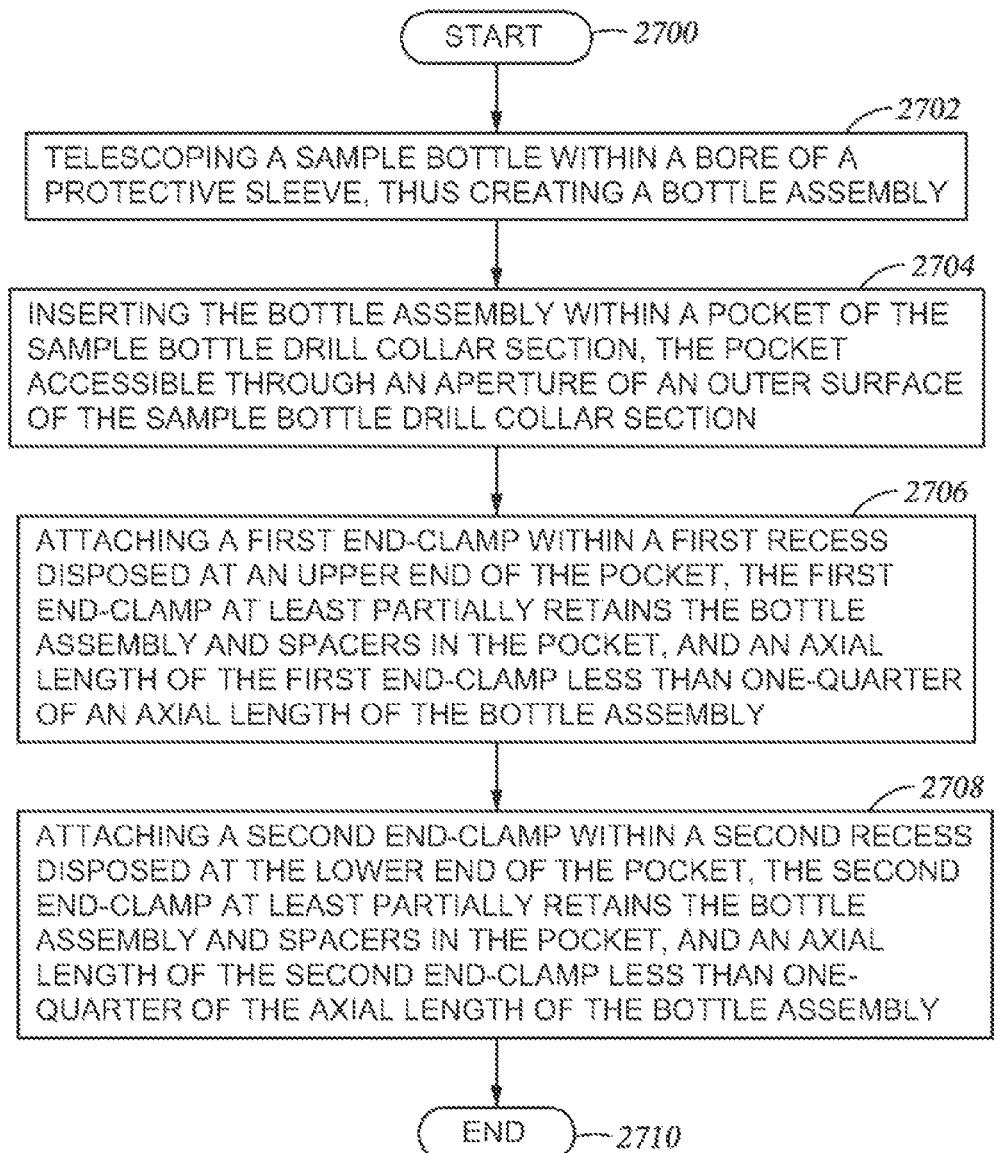
FIG. 27 shows a method in accordance with at least some embodiments.

Finally, FIG. 27 also shows a method in accordance with at least some embodiments. In particular, the method starts (block 2700) and proceeds to telescoping a sample bottle within a bore of a protective sleeve (thus creating a bottle assembly) (block 2702), and then inserting the bottle assembly within a pocket of the sample bottle drill collar section, the pocket accessible through an aperture of an outer surface of the sample bottle drill collar section (block 2704). The method further comprises attaching a first end-clamp within a first recess disposed at an upper end of the pocket, the first end-clamp at least partially retains the bottle assembly and spacers in the pocket, and an axial length of the first end-clamp less than one-quarter of an axial length of the bottle assembly (block 2706). Finally, the illustrative method comprises attaching a second end-clamp within a second recess disposed at the lower end of the pocket, the second end-clamp at least partially retains the bottle assembly and spacers in the pocket, and an axial length of the second end-clamp less than one-quarter of the axial length of the bottle assembly (block 2708), and the method ends (block 2710).

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. An apparatus comprising:
   a drill collar section comprising:
      an outer surface;
      a pocket accessible through an aperture in the outer surface, the pocket defining a first side wall and a second side wall;
      a bottle assembly disposed within the pocket, the bottle assembly comprising a sample bottle having an axial length;
      one or more clamps coupled to the outer surface and abutting or overlapping the bottle assembly, the one or more clamps at least partially retaining the bottle assembly in the pocket; and
      one or more spacers disposed within the pocket, the one or more spacers abutting the bottle assembly and at least one of the first and second side walls of the pocket.

2. The apparatus of claim 1, wherein the one or more clamps comprise:
   an intermediate clamp coupled to the outer surface and spanning the pocket from the first side wall to the second side wall, the intermediate clamp at least partially retaining the bottle assembly in the pocket, and the intermediate clamp having an axial length less than the axial length of the sample bottle.

3. The apparatus of claim 1, wherein the one or more clamps comprise:
   an end-clamp coupled to the outer surface at an end of the pocket, the end-clamp at least partially retaining the bottle assembly in the pocket.

4. The apparatus of claim 1, further comprising:
   a probe that selectively extends beyond the outer surface toward an earth formation, the probe being adapted to draw fluids from the earth formation;
   wherein the bottle assembly is fluidly coupled to the probe.

5. The apparatus of claim 1, wherein the bottle assembly further comprises a sleeve comprising a bore, the sample bottle being disposed within the bore,
   the sleeve having an axial length substantially the same as the sample bottle.

6. The apparatus of claim 5, wherein an outside diameter of the sample bottle defines a circular cross-section and an outside diameter of the sleeve defines a circular cross-section.

7. The apparatus of claim 1, wherein:
the pocket defines a cross-section comprising a bottom portion extending to the first and second side walls, the first and second side walls being spaced in a parallel relation; and
the bottle assembly outside surface defines a conformal surface to the pocket.

8. The apparatus of claim 1, wherein the one or more spacers comprise:
a first spacer disposed within the pocket, the first spacer defining a first portion that abuts the bottle assembly and a second portion that abuts the first side wall of the pocket; and
a second spacer disposed within the pocket, the second spacer defining a first portion that abuts the bottle assembly and a second portion that abuts the second side wall of the pocket;
wherein each of the first and second spacers has an axial length greater than half the axial length of the sample bottle.

9. The apparatus of claim 1, wherein the drill collar section further comprises an epoxy within the pocket, the epoxy abutting the first and second side walls and being coupled to the bottle assembly.

10. A method of assembling a sample bottle drill collar section comprising:
inserting a bottle assembly within a pocket of the sample bottle drill collar section, the pocket defining first and second side walls and being accessible through an aperture of an outer surface of the sample bottle drill collar section, the bottle assembly comprising a sample bottle having an axial length;
attaching one or more clamps to the outer surface of the sample bottle drill collar section, each of the one or more clamps abutting or overlapping the bottle assembly and at least partially retaining the bottle assembly in the pocket; and
inserting one or more spacers within the pocket, the one or more spacers abutting the bottle assembly and at least one of the first and second side walls of the pocket.

11. The method of claim 10, wherein attaching the one or more clamps to the outer surface of the sample bottle drill collar section comprises:
attaching an intermediate clamp to the outer surface, the intermediate clamp spanning the pocket from the first side wall to the second side wall, the intermediate clamp at least partially retaining the bottle assembly in the pocket, and the intermediate clamp having an axial length less than the axial length of the sample bottle.

12. The method of claim 10, wherein attaching the one or more clamps to the outer surface of the sample bottle drill collar section comprises:
attaching an end-clamp to the outer surface at an end of the pocket, the end-clamp at least partially retaining the bottle assembly in the pocket.

13. The method of claim 10, further comprising telescoping the sample bottle within a bore of a protective sleeve, thus creating the bottle assembly;
wherein an outside diameter of the protective sleeve defines a circular cross-section and an outside diameter of the sample bottle defines a circular cross-section.

14. The method of claim 10, wherein inserting the one or more spacers within the pocket comprises:
inserting a first spacer into the pocket such that a first surface of the first spacer abuts the bottle assembly and a second surface of the first spacer abuts the first side wall of the pocket; and
inserting a second spacer into the pocket such that a first surface of the second spacer abuts the bottle assembly and a second surface of the second spacer abuts the second side wall of the pocket.

15. The method of claim 10, wherein, after inserting the bottle assembly within the pocket, the method further comprises:
applying an epoxy over the bottle assembly within the pocket such that at least a portion of the bottle assembly is submerged in the epoxy and the epoxy abuts the first and second side walls of the pocket; and
allowing the epoxy to at least partially cure.

16. An apparatus comprising:
a drill collar section comprising:
an outer surface;
a pocket accessible through an aperture in the outer surface, the pocket defining a first side wall and a second side wall;
a bottle assembly disposed within the pocket, the bottle assembly comprising a sample bottle having an axial length;
one or more clamps coupled to the outer surface and abutting or overlapping the bottle assembly, the one or more clamps at least partially retaining the bottle assembly in the pocket; and
an adhesive within the pocket, the adhesive coupled to the bottle assembly and abutting the bottle assembly and at least one of the first and second side walls.

17. The apparatus of claim 16, wherein the one or more clamps comprise:
an intermediate clamp coupled to the outer surface and spanning the pocket from the first side wall to the second side wall, the intermediate clamp at least partially retaining the bottle assembly in the pocket, and the intermediate clamp having an axial length less than the axial length of the sample bottle.

18. The apparatus of claim 16, wherein the one or more clamps comprise:
an end-clamp coupled to the outer surface at an end of the pocket, the end-clamp at least partially retaining the bottle assembly in the pocket.

19. The apparatus of claim 16, further comprising:
a probe that selectively extends beyond the outer surface toward an earth formation, the probe being adapted to draw fluids from the earth formation;
wherein the bottle assembly is fluidly coupled to the probe.

20. The apparatus of claim 16, wherein the adhesive is, at least in part, an epoxy.

21. The apparatus of claim 16, wherein the bottle assembly further comprises:
a sleeve comprising a central bore, the sample bottle received within the central bore, and the sleeve having an axial length substantially the same as the sample bottle.

22. A method of assembling a sample bottle drill collar section comprising:
inserting a bottle assembly within a pocket of the sample bottle drill collar section, the pocket defining first and second side walls and being accessible through an aperture of an outer surface of the sample bottle drill collar section, the bottle assembly comprising a sample bottle having an axial length;
applying an adhesive adjacent the bottle assembly within the pocket such that the adhesive abuts the bottle assembly and at least one of the first and second side walls of the pocket;

allowing the adhesive to at least partially cure; and attaching one or more clamps to the outer surface of the sample bottle drill collar section, each of the one or more clamps abutting or overlapping the bottle assembly and at least partially retaining the bottle assembly in the pocket.

23. The method of claim 22, wherein attaching the one or more clamps to the outer surface of the sample bottle drill collar section comprises:

attaching an intermediate clamp to the outer surface, the intermediate clamp spanning the pocket from the first side wall to the second side wall, the intermediate clamp at least partially retaining the bottle assembly in the pocket, and the intermediate clamp having an axial length less than the axial length of the sample bottle.

24. The method of claim 22, wherein attaching the one or more clamps to the outer surface of the sample bottle drill collar section comprises:

attaching an end-clamp to the outer surface at an end of the pocket, the end-clamp at least partially retaining the bottle assembly in the pocket.

25. The method of claim 24, wherein applying the adhesive further comprises applying the adhesive such that bottle assembly is submerged between the intermediate clamp and the end-clamp.

26. The method of claim 22, wherein applying the adhesive further comprises applying an adhesive that comprises, at least in part, an epoxy.

27. The method of claim 22, wherein prior to inserting the bottle assembly, the method further comprises telescoping a sample bottle within a bore of a protective sleeve, thus creating the bottle assembly.

* * * * *